US009733221B2

(12) United States Patent
Zimmermann et al.

(10) Patent No.: US 9,733,221 B2
(45) Date of Patent: Aug. 15, 2017

(54) INJECTION NEEDLE CARTRIDGE WITH INTEGRATED SEALING FORCE GENERATOR

(71) Applicant: Agilent Technologies, Inc., Loveland, CA (US)

(72) Inventors: Hans-Peter Zimmermann, Waldbronn (DE); David Jenaro, Nufringen (DE)

(73) Assignee: Agilent Technologies, Inc., Santa Clara, CA (US)

( * ) Notice: Subject to any disclaimer, the term of this patent is extended or adjusted under 35 U.S.C. 154(b) by 565 days.

(21) Appl. No.: 14/264,755

(22) Filed: Apr. 29, 2014

(65) Prior Publication Data

US 2014/0318274 A1    Oct. 30, 2014

Related U.S. Application Data

(63) Continuation-in-part of application No. 14/124,908, filed as application No. PCT/EP2011/059644 on Jun. 9, 2011.

(30) Foreign Application Priority Data

Jul. 8, 2013    (GB) .................................. 1312181.9

(51) Int. Cl.
   *G01N 30/24*    (2006.01)
   *B01D 15/14*    (2006.01)

(52) U.S. Cl.
   CPC ............. *G01N 30/24* (2013.01); *B01D 15/14* (2013.01)

(58) Field of Classification Search
   CPC ... G01N 30/24; G01N 2030/167; B01D 15/14
   See application file for complete search history.

(56) References Cited

U.S. PATENT DOCUMENTS 4,974,458 A * 12/1990 Koike ...................... G01N 1/28
                                                    73/864.25
4,982,597 A    1/1991 Berger
(Continued)

FOREIGN PATENT DOCUMENTS

CN        101925822 A      12/2010
DE      102007000622        5/2008
(Continued)

OTHER PUBLICATIONS

Office action dated Mar. 7, 2016 from related U.S. Appl. No. 14/124,908.
(Continued)

*Primary Examiner* — Paul West

(57) ABSTRACT

An injection needle cartridge for a sample injector for injecting a sample fluid into a mobile phase in a fluidic path of a fluid separation system between a mobile phase drive and a separation unit, the injection needle cartridge comprising an injection needle configured for aspirating the sample fluid from a fluid container when the injection needle has been moved to the fluid container, and for injecting aspirated sample fluid into the fluidic path when the injection needle is sealingly accommodated in a needle seat, and a sealing force generator configured for applying a sealing force to the injection needle for sealingly accommodating the injection needle in the needle seat, wherein the injection needle cartridge is configured for being substitutably mountable on a handling robot of the sample injector for handling the injection needle cartridge between the fluid container and the needle seat.

27 Claims, 25 Drawing Sheets

(56) References Cited

U.S. PATENT DOCUMENTS

| | | | |
|---|---|---|---|
| 5,305,650 | A | 4/1994 | Koike et al. |
| 5,805,454 | A | 9/1998 | Valerino et al. |
| 6,148,680 | A | 11/2000 | Baeuerle et al. |
| 7,138,050 | B2 | 11/2006 | Maruyama et al. |
| 7,555,937 | B2 | 7/2009 | Hirayama et al. |
| 7,635,326 | B2 | 12/2009 | Gueller et al. |
| 2006/0259195 | A1 | 11/2006 | Eliuk et al. |
| 2007/0095158 | A1* | 5/2007 | Maeda ............... G01N 35/1095 73/864 |
| 2010/0037919 | A1 | 2/2010 | Doebelin et al. |
| 2011/0120237 | A1 | 5/2011 | Leroi et al. |

FOREIGN PATENT DOCUMENTS

| | | |
|---|---|---|
| DE | 102008041863 | 4/2009 |
| DE | 102008041863 A1 | 4/2009 |
| EP | 309596 | 4/1989 |
| EP | 0990899 | 4/2000 |
| EP | 1366822 | 3/2003 |
| EP | 1577004 | 9/2005 |
| EP | 2166361 A2 | 3/2010 |

OTHER PUBLICATIONS

Non-Final Office action dated Aug. 25, 2016, from related U.S. Appl. No. 14/124,908.
Machine translation of DE102008041863A1, published Apr. 9, 2009.
Machine translation of EP2166361, published Mar. 24, 2010.
Office Action mailed Jul. 14, 2015 in Chinese Application No. 201180071530.X (Unofficial/Non-certified translation provided by foreign agent included).
Drexler, et al. "Improvements to the Sample Manipulation Design of a LEAP CTC HTS PAL Autosampler Used for High-Throughput Qualitative and Quantitative Liquid Chromatogrphy—Mass Spectrometry Assays", Journal of the Association for Laboratory Automation, Elsevier, vol. 12, No. 3 XP022078345 ISSN: 1535-5535, DOI: 10.1016/J.JALA.2007.01.002 p. 154, right-hand column; figure 3b p. 154, left-hand column.
Invitation to Pay Additional Fees and Partial Search Report mailed Mar. 2, 2012 in International Patent Application No. PCT/EP2011/059644.
International Search Report and Written Opinion mailed May 10, 2012 in International Patent Application No. PCT/EP2011/059644.
Notice of Decision to Grant Received dated May 4, 2017 from related Chinese Application No. 201180071530.X.

* cited by examiner

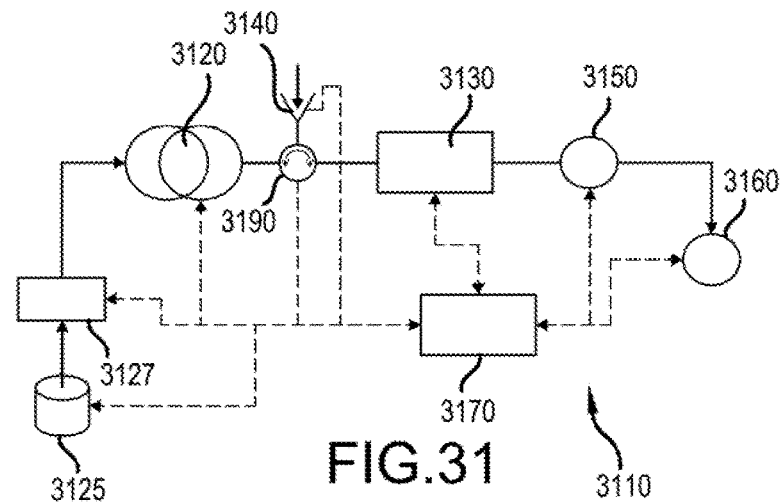
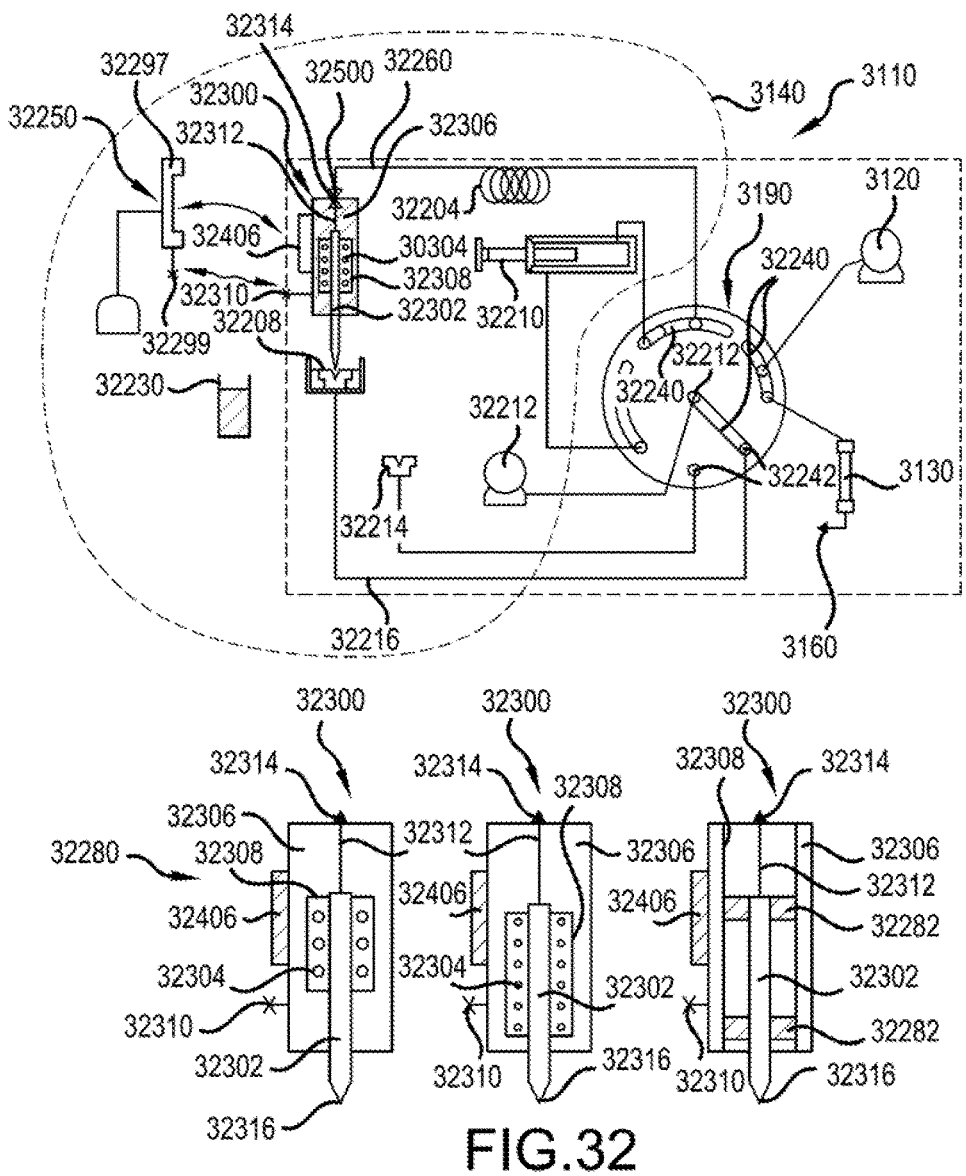

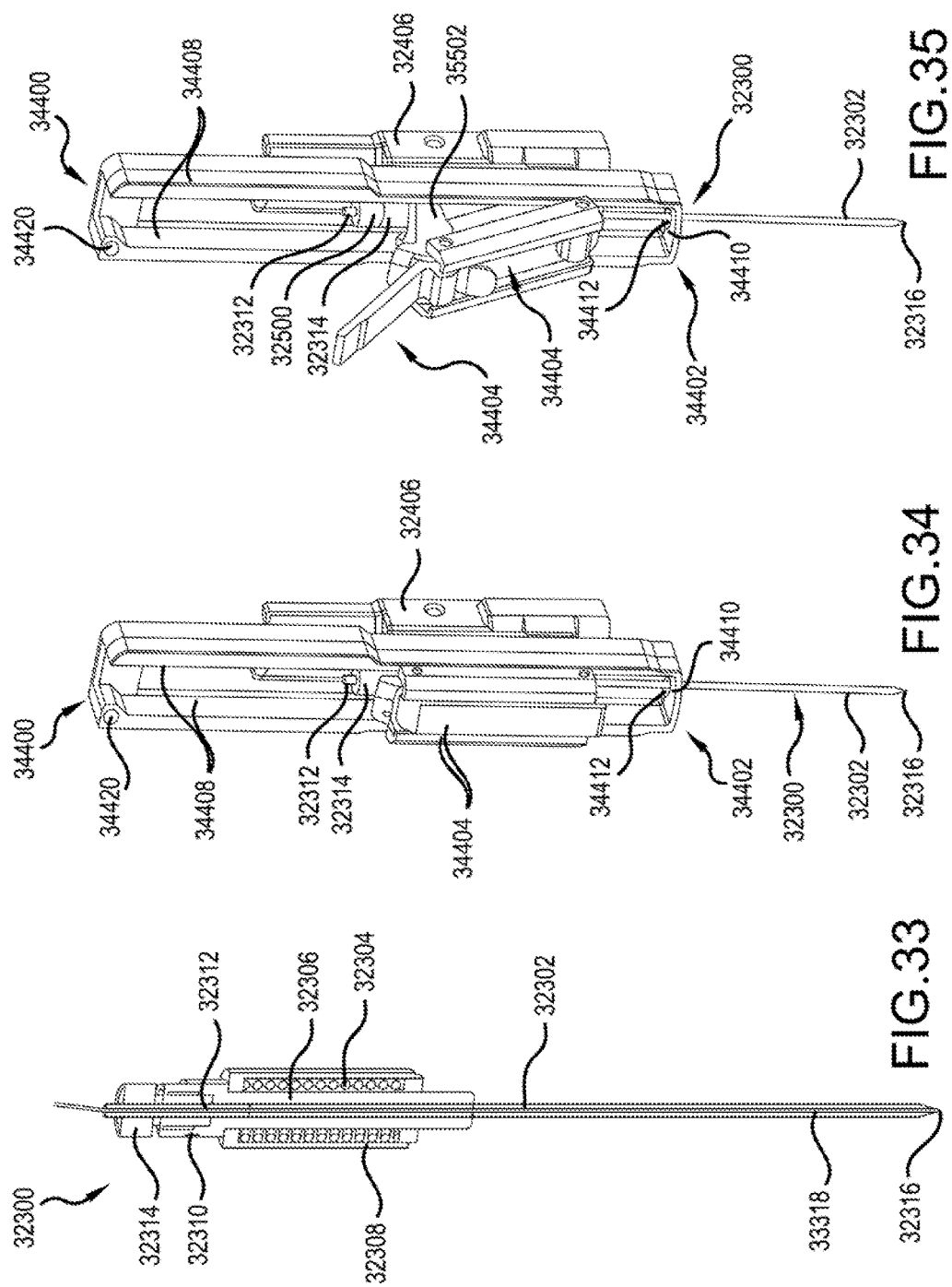

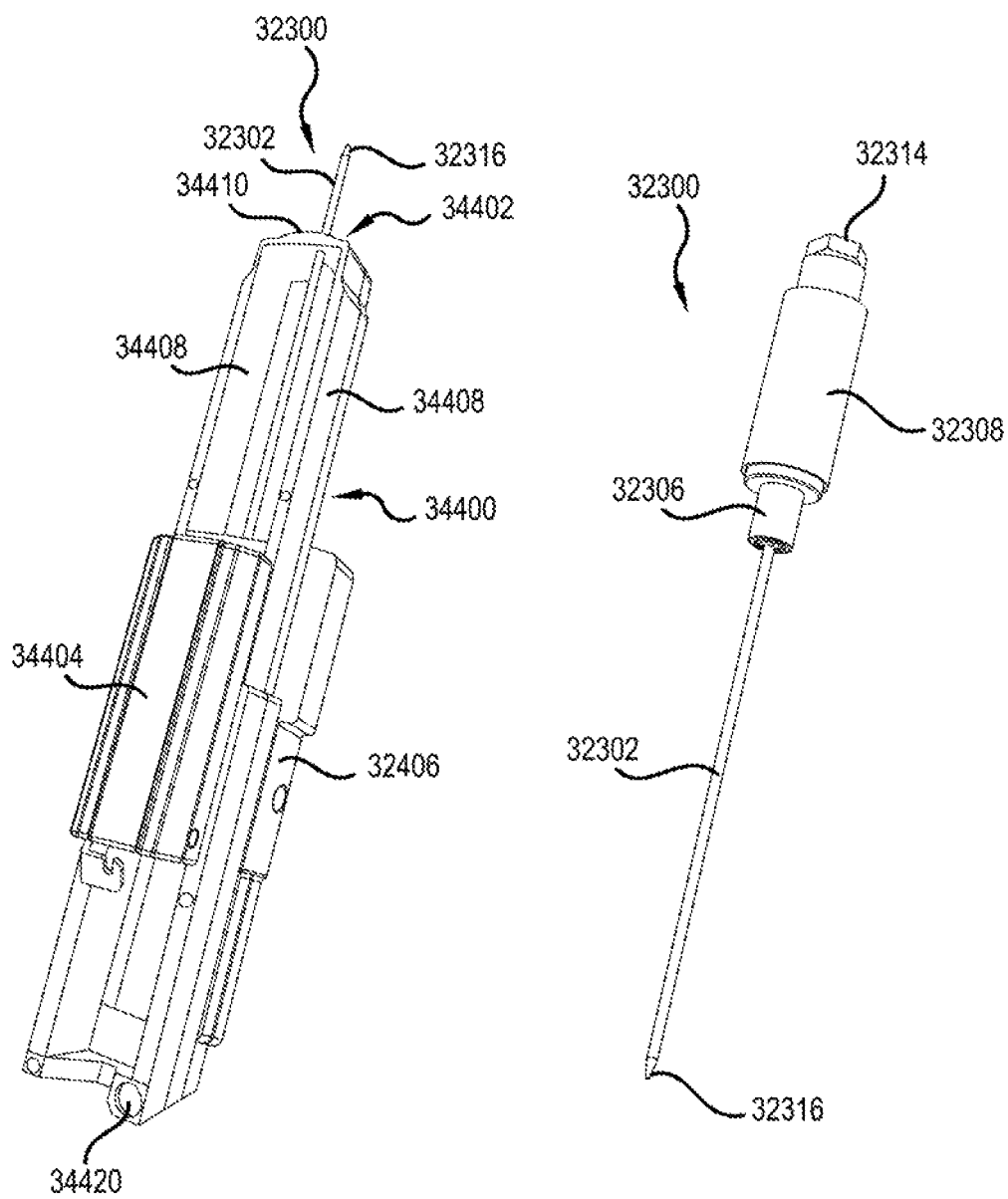

INJECTION NEEDLE CARTRIDGE WITH INTEGRATED SEALING FORCE GENERATOR

CROSS-REFERENCE TO RELATED APPLICATIONS

The present application is a continuation-in-part of and claims priority under 35 U.S.C. §120 from U.S. patent application Ser. No. 14/124,908 entitled "SAMPLE INJECTOR WITH DISCONNECTABLE INJECTION NEEDLE" to Hans-Peter Zimmerman and filed on Dec. 9, 2013, which is a National Phase Application of International Application No. PCT/EP2011/05964 filed on Jun. 9, 2011. The present application claims priority under 35 U.S.C. §119 from GB Patent Application No. 1312181.9 entitled "INJECTION NEEDLE CARTRIDGE WITH INTEGRATED SEALING FORCE GENERATOR" and filed on Jul. 8, 2013. The entire disclosures of these U.S., GB, and International Patent Applications are specifically incorporated herein by reference.

BACKGROUND

In liquid chromatography, a fluidic sample and an eluent (liquid mobile phase) may be pumped through conduits and a column in which separation of sample components takes place. In a sample loop, the sample may be injected into a fluidic path by a mechanically drivable needle. The drivable needle is controllable to be moved out of a seat of the sample loop into a vial or any other fluid container to receive a fluid and back from the vial into the seat. The column may comprise a material which is capable of separating different components of the fluidic analyte. Such a material, so-called beads which may comprise silica gel, may be filled into a column tube which may be connected downstream to other components, such as a detector, a fractioner, a waste, etc., by conduits.

An autosampler can be used in liquid chromatography applications, and comprises an injection needle and a corresponding needle seat. In certain known autosamplers, a robot grips the needle and inserts the needle into the needle seat, wherein the robot applies a sealing force to achieve a high pressure resistant sealing between needle and needle seat. When different kinds of needles are used for different applications, the robot has to apply sealing forces of different values to the needle-seat arrangement. For instance, when a ceramic needle for biological applications is used, another sealing force is required as compared to a scenario in which a stainless steel needle is used. This requires to program or adjust the robot in a way that different needle force values can be applied depending on the used needle. Thus, in conventional systems, the injection needle is mounted to a robot arm and is pressed into the sealing seat with a fixed force. The sealing force is defined by a loading spring inside the robot arm. Hence, the sealing force is defined by the robot system. If an injection needle is used with different material or sealing geometry (for instance bioinert, 600 bar-resistant, 1200 bar-resistant), the sealing force has to be changed via firmware or software of the needle drive. Hence, proper sealing between an injection needle and a needle seat is still a challenge, particularly when a high degree of flexibility is desired to use such a system for different applications.

What is needed is a device that enables efficient fluid handling in a separation system.

SUMMARY

According to an exemplary embodiment, an injection needle cartridge (such as a separate module) for a sample injector for injecting a sample fluid into a mobile phase in a fluidic path of a fluid separation system between a mobile phase drive and a separation unit is provided, wherein the injection needle cartridge comprises an injection needle configured for aspirating the sample fluid from a fluid container when the injection needle has been moved to the fluid container, and for injecting aspirated sample fluid into the fluidic path when the injection needle is sealingly accommodated in a needle seat, and a sealing force generator configured for generating and applying a sealing force to the injection needle for sealingly accommodating the injection needle in the needle seat, wherein the injection needle cartridge is configured for being substitutably or exchangeably mountable on a handling robot of the sample injector for handling the injection needle cartridge between the fluid container and the needle seat.

According to another exemplary embodiment, a needle set is provided which comprises a plurality of injection needle cartridges having the above mentioned features, wherein different ones of the injection needle cartridges provide different sealing force values (however, a part of the injection needle cartridges may also provide the same sealing force value).

According to still another exemplary embodiment, a sample injector for injecting a sample fluid into a mobile phase in a fluidic path of a fluid separation system between a mobile phase drive and a separation unit is provided, wherein the sample injector comprises an injection needle cartridge having the above mentioned features, a needle seat configured for sealingly accommodating the injection needle of the injection needle cartridge and providing fluid communication with the fluidic path, wherein the sealing force generator of the injection needle cartridge provides the sealing force when the injection needle is accommodated in the needle seat, and a handling robot on which the injection needle cartridge is mountable or mounted and being configured for moving the injection needle between a fluid container containing the sample fluid and the needle seat.

According to still another exemplary embodiment, a fluid separation system (such as a liquid chromatography system) for separating compounds of a sample fluid in a mobile phase is provided, wherein the fluid separation system comprises a mobile phase drive, preferably a pumping system, configured to drive the mobile phase through the fluid separation system, a separation unit, preferably a chromatographic column, configured for separating compounds of the sample fluid in the mobile phase, and a sample injector having the above mentioned features and being configured for injecting the sample fluid in the fluidic path between the mobile phase drive and the separation unit.

According to yet another exemplary embodiment, a method of operating a sample injector with an injection needle cartridge having the above mentioned features for injecting a sample fluid into a mobile phase in a fluidic path of a fluid separation system between a mobile phase drive and a separation unit is provided, wherein the method comprises substitutably mounting the injection needle cartridge on a handling robot of the sample injector, moving the injection needle cartridge by the handling robot to a fluid container containing the sample fluid, aspirating the sample fluid from the fluid container via the injection needle into a sample loop of the sample injector, moving the injection needle cartridge by the handling robot to the needle seat and sealingly accommodating the injection needle in the needle seat by applying a sealing force generated by the sealing force generator, and injecting the aspirated sample fluid into the fluidic path when the injection needle is sealingly accommodated in the needle seat.

According to an embodiment, an integral injection needle cartridge is provided as a separate member from robot and needle seat and having integrated therein a sealing force generator for generating a precisely defined value of a sealing force to be applied to the needle cartridge-seat configuration, which value is specifically adapted to the present application as well as to the kind of injection needle being integrated as well in the injection needle cartridge. Thus, for each specific application, a user only has to select an appropriate needle cartridge having a needle with desired properties (e.g. ceramic needle or stainless steel needle) to ensure that the correct value of the sealing force is applied to the cartridge-seat configuration. No inconsistencies between robot and needle can occur. Furthermore, any inaccuracies concerning a sealing force being transmitted between robot and needle can be excluded when the sealing force generator forms part of a (for instance inseparable) injection needle cartridge, since no sealing force transmission is necessary between robot and needle according to exemplary embodiments. Thus, a flexible modular needle cartridge is provided in which a predefined, appropriate sealing force is generated which may be adjusted to the individual needle geometry. An exemplary embodiment therefore provides a needle cartridge system, in which a preloaded spring or another appropriate sealing force generator is included in the cartridge which determines the sealing force of the specific needle. If the needle has to be changed in such a system (for instance a liquid chromatography system, in which the injection needle is a consumable), the complete needle cartridge including sealing force generator and housing (e.g. spring and spring cage) may be changed. Therefore, the sealing force can be adapted to the requirements of the needle material, needle geometry and maximum system pressure without changing the algorithm of a needle drive mechanism. Hence, exemplary embodiments have the advantage that the sealing force is an attribute of the needle cartridge rather than of the robot arm. Different types of needle cartridges can thus be handled by the same needle drive mechanism.

In the following, further embodiments of the injection needle cartridge, the needle set, the sample injector, the fluid separation system, and the method will be explained.

In an embodiment, the injection needle cartridge comprises a housing accommodating at least part of the injection needle and at least part of the sealing force generator. Such a housing may serve as a mechanical protection of the sealing force generator, guaranteeing its accuracy in terms of the generated sealing force value and direction, as well as of the needle and may ensure a proper cooperation of these components.

In an embodiment, the sealing force generator comprises an elastic member, particularly one of the group consisting of a sealing force spring and an elastomeric element, configured for applying the sealing force to the injection needle. The term "elastic member" may denote a physical structure which intrinsically generates a back driving force proportional to an elongation distance (i.e. a length change in response to a compression or an expansion) thereof upon applying an elongation force. For instance, a spring showing a behavior according to Hooke's law is considered as an elastic member. Another example for an elastic member is a flexible rod made of an elastomeric material. Such a sealing force generator is simple in construction and is capable of applying a precisely defined sealing force between needle and seat.

In an embodiment, at least part of the sealing force spring (particularly a helical spring) is arranged to circumferentially surround at least part of the injection needle. This allows to manufacture the injection needle cartridge in a compact way since at least part of the injection needle may be accommodated within the interior volume of a helical spring or the like.

In an embodiment, the elastic member is supported between the injection needle and the housing. For instance, one end of the elastic member may be mounted or supported fixedly on the housing, whereas the opposing other end can be fixed directly or indirectly to the injection needle so that in response to compressing the elastic member by pressing the needle against the seat, the spring is pressed against the housing and applies a counterforce to the needle with a direction to press the needle apart from the housing and against the seat.

In an embodiment, the elastic member is mounted in a pre-biased state in the injection needle cartridge. Thus, the elastic member may be pre-compressed or pre-expanded (even in the absence of a pressure applied from the needle to the seat) so that even when the injection needle is presently not pressed into the seat, the elastic member is already under tension. This further strengthens the pressure tight connection between needle and seat because the pre-tensioning of the elastic member further promotes the sealing between needle and seat.

In an embodiment, the sealing force generator comprises one of the group consisting of a magnetic sealing force generator generating a magnetic sealing force, and an electric sealing force generator generating an electric sealing force. Thus, the sealing force needs not necessarily be generated by a mechanical mechanism or a mechanical mechanism alone. Additionally or alternatively, it is also possible to use the repelling force of two or more spaced magnetic elements (such as permanent magnets), one of which being connected to the housing, and the other one being attached to the needle. When the needle is then pressed into the seat and the needle is consequently moved relative to the housing, the distance between the two magnetic elements is reduced which results in the generation of a back driving counterforce acting on the needle. This sealingly presses the needle in a fluid tight and pressure tight manner into the seat. Additionally or alternatively, even attracting magnetic elements or members generating electric forces can be used for providing the sealing force.

In an embodiment, the injection needle cartridge comprises a readable marker being indicative of at least one property of the injection needle cartridge (for instance a type of the injection needle cartridge, its needle, its pressure resistance, its size, etc.). Preferably, the marker may be indicative of a sealing force value provided by the sealing force generator.

In an embodiment, the readable marker comprises a machine-readable marker, particularly one of the group consisting of a barcode and a radio frequency identification tag (RFID tag). Correspondingly, the robot or another member of the sample injector may be equipped with a corresponding reader device such as a barcode reader or an RFID reader. Therefore, it may be made possible for the robot arm or another member of the sample injector to read out the marker to determine which kind of the sealing force and which kind of corresponding injection needle are implemented in the "black box" like injection needle cartridge being configured as a module replaceable as a whole. By equipping the housing of the injection needle cartridge with such a machine-readable marker, the needle drive mechanism of the robot can automatically determine which injection needle cartridge is presently used. If necessary, the needle drive mechanism can then self-adjust its operation in accordance with the presently used injection needle cartridge. Therefore, the sample injector can be synchronized or coordinated so as to prevent an erroneous operation.

In an embodiment, the readable marker comprises a human-readable marker, particularly one of the group consisting of an alphanumeric code and a color marker. For example, the different types of needle cartridges may be color-coded, wherein different colors may be used for example for the cartridge housing (such as a spring cage when using a spring as sealing force generator) of different injection needle cartridges. This allows to visualize the type of needle to a user so as to prevent the use of an inappropriate needle for a certain application.

In an embodiment, the injection needle cartridge comprises a capillary in fluid communication with the injection needle. Such a capillary, which may be at least partially formed within the housing of the cartridge, can then provide for fluid communication of the needle with a sample loop of the sample injector.

In an embodiment, the injection needle cartridge comprises a fitting member in fluid communication with the injection needle and being configured to form a fluid-tight and fluid communicating fitting upon being connected with a corresponding fitting member counterpart in fluid communication with a loop capillary of the sample injector. Such a fitting member of the injection needle cartridge may be a male fitting member or a female fitting member being connected with a corresponding inverse female fitting member or male fitting member, respectively, as the fitting member counterpart. The correspondingly formed fitting may be a high pressure resistant fluid tight fitting. The connection between the two cooperating fitting members may be performed with a bayonet connection, a snap-in connection, a screwing connection, etc. By such a fitting, the injection needle cartridge may be brought in fluid communication with the rest of the sample injector.

In an embodiment, the sealing force generator is configured for applying a sealing force with a predefined value and with a predefined direction (preferably along an extension direction of the needle) when the injection needle is accommodated in the needle seat. Therefore, the value and the vector direction of the sealing force may be an intrinsic property of the injection needle cartridge and may be independently of other components such as the robot. Therefore, a very precise adjustment of the sealing force can be ensured.

In an embodiment, the needle set comprises at least one ceramic needle, and at least one metallic needle. The ceramic needle may for example be used for biological applications. The metallic needle can be used as a standard needle. It can be made of stainless steel, platinum, etc. It is also possible that the set comprises other needles made of other materials, such as plastic.

It is furthermore possible that the needle set comprises different injection needle cartridges capable to withstand different pressure values. For example, one injection needle cartridge may be made for applications up to 600 bar, another one may be configured for applications of up to 1200 bar. The value of the sealing force may be adjusted correspondingly.

In an embodiment, the sample injector comprises a cartridge adapter configured for detachably receiving the injection needle cartridge and being configured for being attached to the handling robot. The cartridge adapter forms a mechanic interface between the injection needle cartridge and the robot.

In an embodiment, the cartridge adapter comprises a needle protection mechanism configured for operating the injection needle selectively in a protected (for instance retracted) state in which at least a tip of the injection needle is accommodated within the cartridge adapter or in an active (for instance expanded) state in which at least the tip of the injection needle protrudes beyond the cartridge adapter. Therefore, a user can be prevented from being injured by the sharp needle when the latter is accommodated fully within the cartridge adapter. Additionally, the needle can be prevented from damage by protecting it within the cartridge adapter. On the other hand, when the needle is in an active operation mode, it may protrude over the cartridge adapter so as to be capable to immerse into a fluid container or to be inserted into the needle seat.

In an embodiment, the needle protection mechanism is configured for forcing the injection needle into the protected state (automatically or by user operation) upon disassembling the injection needle cartridge from the handling robot and/or for forcing the injection needle into the active state (automatically or by user operation) upon mounting the injection needle cartridge on the handling robot.

In an embodiment, the cartridge adapter comprises a cartridge locking mechanism configured for detachably locking the injection needle cartridge to the cartridge adapter. For instance, it may be realized by a lever-based clamping mechanism for detachably locking the injection needle cartridge by a latch. Therefore, the injection needle cartridge can be connected by a quick lock system of the cartridge adapter (for instance by merely inserting the injection needle cartridge into the cartridge adapter and by subsequently pivoting a lever) on the needle drive system (particularly on a robot arm thereof). When the cartridge is inserted into a needle holder of the cartridge adapter it can be clamped with a latch so that no tooling is needed for a user to change the needle.

In an embodiment, the injection needle cartridge comprises a robot connection element laterally connected at the housing and configured for attaching the injection needle cartridge to the handling robot by sliding the robot connection element on the handling robot. Thus, the robot connection element may be integrated into the needle cartridge. This provides for very compact configuration.

In an alternative embodiment, the sample injector comprises a robot connection element laterally connected at the cartridge adapter and configured for attaching the cartridge adapter to the handling robot by sliding the robot connection element on the handling robot (wherein the robot connection element may be locked to the handling robot upon sliding). Hence, assembling and disassembling the injection needle cartridge (which is necessary regularly in view of the fact that the injection needle cartridge is a consumable) via the robot connection element to the robot can be performed with a very simple procedure.

In an embodiment, the sample injector comprises a needle set having the above mentioned features, wherein the cartridge adapter may be configured for detachably receiving each of the injection needle cartridges. Therefore, a multipurpose sample injector can be provided in which only one appropriate of several injection needle cartridges needs to be selected at a time for use with the rest of the sample injector to meet the requirements of a corresponding application.

In an embodiment, the sealing force generator, the injection needle and the needle seat are configured to cooperate so that the injection needle is accommodatable in the needle seat in a high pressure-tight manner, particularly pressure-tight at a pressure of about 1200 bar. Such an injection needle cartridge meets requirements of modern liquid chromatography applications.

In an embodiment, the handling robot is free of a sealing force generator for generating a sealing force for sealingly accommodating the injection needle of the injection needle cartridge in the needle seat. Therefore, the handling robot can be formed in a compact way and capable of serving injection needle cartridges for very different applications.

The separation unit may be filled with a separating material. Such a separating material which may also be denoted as a stationary phase may be any material which allows an adjustable degree of interaction with a sample fluid so as to be capable of separating different components of such a sample fluid. The separating material may be a liquid chromatography column filling material or packing material comprising at least one of the group consisting of polystyrene, zeolite, polyvinylalcohol, polytetrafluorethylene, glass, polymeric powder, silicon dioxide, and silica gel, or any of above with chemically modified (coated, capped etc) surface. However, any packing material can be used which has material properties allowing an analyte passing through this material to be separated into different components, for instance due to different kinds of interactions or affinities between the packing material and fractions of the analyte.

At least a part of the separation unit may be filled with a fluid separating material, wherein the fluid separating material may comprise beads having a size in the range of essentially 1 µm to essentially 50 µm. Thus, these beads may be small particles which may be filled inside the separation section of the microfluidic device. The beads may have pores having a size in the range of essentially 0.01 µm to essentially 0.2 µm. The fluidic sample may be passed through the pores, wherein an interaction may occur between the fluidic sample and the pores.

The separation unit may be a chromatographic column for separating components of the fluidic sample. Therefore, exemplary embodiments may be particularly implemented in the context of a liquid chromatography apparatus.

The fluid separation system may be configured to conduct a liquid mobile phase through the separation unit. As an alternative to a liquid mobile phase, a gaseous mobile phase or a mobile phase including solid particles may be processed using the fluid separation system. Also materials being mixtures of different phases (solid, liquid, gaseous) may be processed using exemplary embodiments. The fluid separation system may be configured to conduct the mobile phase through the system with a high pressure, particularly of at least 600 bar, more particularly of at least 1200 bar.

The fluid separation system may be configured as a microfluidic device. The term "microfluidic device" may particularly denote a fluid separation system as described herein which allows to convey fluid through microchannels having a dimension in the order of magnitude of less than 500 µm, particularly less than 200 µm, more particularly less than 100 µm or less than 50 µm or less.

Exemplary embodiments may be implemented in a sample injector of a liquid chromatography apparatus which sample injector may take up a sample fluid from a fluid container and may inject such a sample fluid in a conduit for supply to a separation column. During this procedure, the sample fluid may be compressed from, for instance, normal pressure to a higher pressure of, for instance several hundred bars or even 1000 bar and more. An autosampler may automatically inject a sample fluid from the vial into a sample loop. A tip or needle of the autosampler may dip into a fluid container, may suck fluid into the capillary and may then drive back into a seat to then, for instance via a switchable fluidic valve, inject the sample fluid towards a sample separation section of the liquid chromatography apparatus.

The fluid separation system may be configured to analyze at least one physical, chemical and/or biological parameter of at least one component of the sample fluid in the mobile phase. The term "physical parameter" may particularly denote a size or a temperature of the fluid. The term 'chemical parameter' may particularly denote a concentration of a fraction of the analyte, an affinity parameter, or the like. The term "biological parameter" may particularly denote a concentration of a protein, a gene or the like in a biochemical solution, a biological activity of a component, etc.

The fluid separation system may be implemented in different technical environments, like a sensor device, a test device, a device for chemical, biological and/or pharmaceutical analysis, a capillary electrophoresis device, a liquid chromatography device, a gas chromatography device, an electronic measurement device, or a mass spectroscopy device. Particularly, the fluid separation system may be a High Performance Liquid Chromatography (HPLC) device by which different fractions of an analyte may be separated, examined and analyzed.

An embodiment of the present invention comprises a fluid separation system configured for separating compounds of a sample fluid in a mobile phase. The fluid separation system comprises a mobile phase drive, such as a pumping system, configured to drive the mobile phase through the fluid separation system. A separation unit, which can be a chromatographic column, is provided for separating compounds of the sample fluid in the mobile phase. The fluid separation system may further comprise a sample injector configured to introduce the sample fluid into the mobile phase, a detector configured to detect separated compounds of the sample fluid, a collector configured to collect separated compounds of the sample fluid, a data processing unit configured to process data received from the fluid separation system, and/or a degassing apparatus for degassing the mobile phase.

Embodiments of the present invention might be embodied based on most conventionally available HPLC systems, such as the Agilent 1290 Series Infinity system, Agilent 1200 Series Rapid Resolution LC system, or the Agilent 1100 HPLC series (all provided by the applicant Agilent Technologies—see www.agilent.com—which shall be incorporated herein by reference).

One embodiment comprises a pumping apparatus having a piston for reciprocation in a pump working chamber to compress liquid in the pump working chamber to a high pressure at which compressibility of the liquid becomes noticeable, One embodiment comprises two pumping apparatuses coupled either in a serial or parallel manner.

The mobile phase (or eluent) can be either a pure solvent or a mixture of different solvents. It can be chosen e.g. to minimize the retention of the compounds of interest and/or the amount of mobile phase to run the chromatography. The mobile phase can also been chosen so that the different compounds can be separated effectively. The mobile phase might comprise an organic solvent like e.g. methanol or acetonitrile, often diluted with water. For gradient operation water and organic is delivered in separate bottles, from which the gradient pump delivers a programmed blend to the system. Other commonly used solvents may be isopropanol, THF, hexane, ethanol and/or any combination thereof or any combination of these with aforementioned solvents.

The sample fluid might comprise any type of process liquid, natural sample like juice, body fluids like plasma or it may be the result of a reaction like from a fermentation broth.

The fluid is preferably a liquid but may also be or comprise a gas and/or a supercritical fluid.

The pressure in the mobile phase might range from 2-200 MPa (20 to 2000 bar), in particular 10-150 MPa (100 to 1500 bar), and more particular 50-120 MPa (500 to 1200 bar).

BRIEF DESCRIPTION OF DRAWINGS

The illustrative embodiments are best understood from the following detailed description when read with the accompanying drawing figures. It is emphasized that the various features are not necessarily drawn to scale. In fact, the dimensions may be arbitrarily increased or decreased for clarity of discussion. Wherever applicable and practical, like reference numerals refer to like elements.

FIG. 31 shows a liquid separation device, in accordance with embodiments of the present invention, e.g. used in high performance liquid chromatography (HPLC).

FIG. 32 illustrates a sample injector of the liquid separation device of FIG. 1 having a set of injection needle cartridges according to an exemplary embodiment.

FIG. 33 illustrates a cross-sectional view of an injection needle cartridge according to an exemplary embodiment.

FIG. 34 illustrates a cartridge adapter of a sample injector according to an exemplary embodiment receiving the injection needle cartridge of FIG. 3 in a locked state.

FIG. 35 illustrates the cartridge adapter of FIG. 4 receiving the injection needle cartridge of FIG. 3 in an unlocked state.

FIG. 36 illustrates a cartridge adapter for receiving an injection needle cartridge together with a robot connection element according to an exemplary embodiment in an operation mode in which the injection needle is exposed to an environment.

FIG. 37 shows a three-dimensional view of the injection needle cartridge implemented in FIG. 36.

DETAILED DESCRIPTION

In the following detailed description, for purposes of explanation and not limitation, specific details are set forth in order to provide a thorough understanding of illustrative embodiments according to the present teachings. However, it will be apparent to one having ordinary skill in the art having had the benefit of the present disclosure that other embodiments according to the present teachings that depart from the specific details disclosed herein remain within the scope of the appended claims. Moreover, descriptions of well-known apparatuses and methods may be omitted so as to not obscure the description of the illustrative embodiments. Such methods and apparatuses are clearly within the scope of the present teachings.

Notably, certain components of the representative embodiments may comprise one or more processing devices. The processing device may be implemented by a computer processor, application specific integrated circuits (ASICs), field-programmable gate arrays (FPGAs), or combinations thereof, using software, firmware, hard-wired logic circuits, or combinations thereof. When using a computer processor, a memory device (not shown) may be included for storing executable software/firmware and/or executable code that allows it to perform the various functions. The memory may include any number, type and combination of random access memory (RAM) and read-only memory (ROM), for example. More generally, software instructions may be stored on a non-transitory computer readable medium and/or executed by one or more processing devices.

Figure 1:
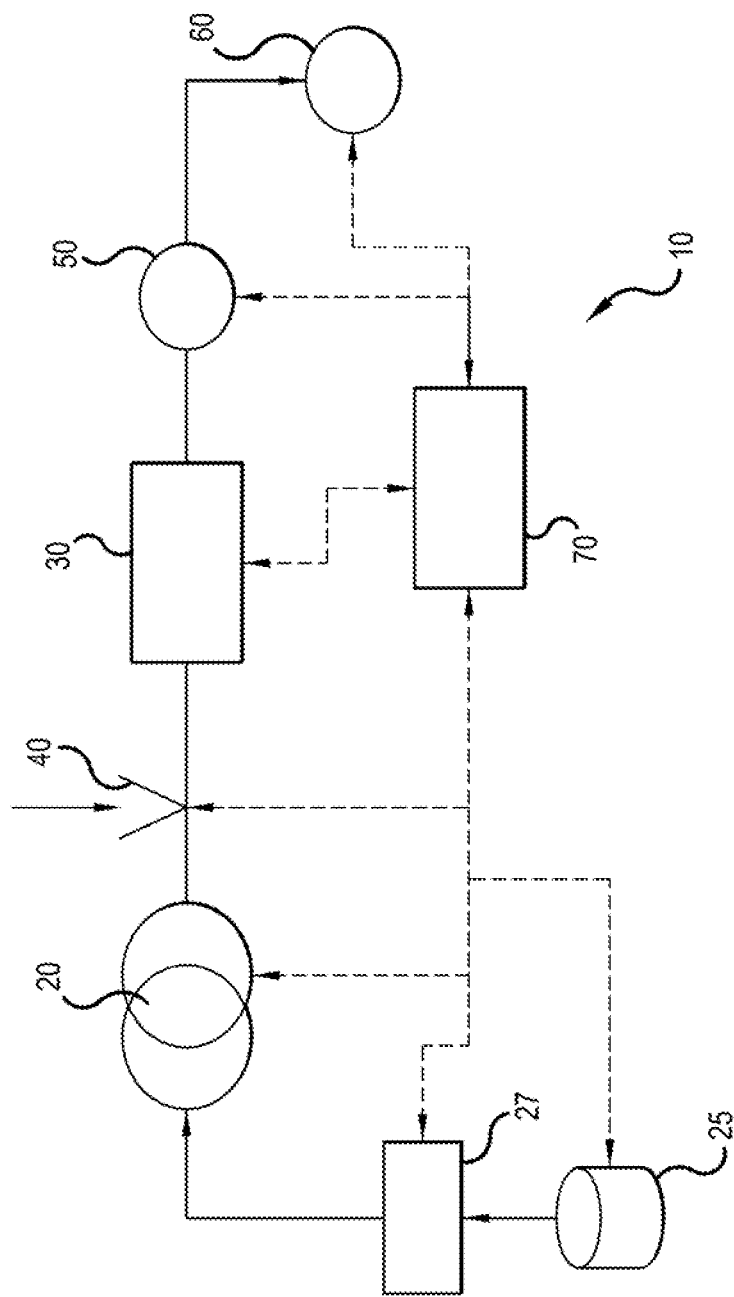
FIG. 1 shows a liquid separation device, in accordance with embodiments of the present invention, e.g. used in high performance liquid chromatography (HPLC).

Referring now in greater detail to the drawings, FIG. 1 depicts a general schematic of a fluid separation system 10. A pump 20 receives a mobile phase from a solvent supply 25, typically via a degasser 27, which degases and thus reduces the amount of dissolved gases in the mobile phase. The pump 20—as a mobile phase drive—drives the mobile phase through a separating device 30 (such as a chromatographic column) comprising a stationary phase. A sampling unit 40 (having a needle/seat arrangement depicted in FIG. 1 schematically) is provided between the pump 20 and the separating device 30 in order to subject or add (often referred to as sample introduction) a sample fluid into the mobile phase. The stationary phase of the separating device 30 is configured for separating compounds of the sample liquid. A detector 50 is provided for detecting separated compounds of the sample fluid. A fractionating unit 60 can be provided for outputting separated compounds of sample fluid.

While the mobile phase can be comprised of one solvent only, it may also be mixed from plural solvents. Such mixing might be a low pressure mixing and provided upstream of the pump 20, so that the pump 20 already receives and pumps the mixed solvents as the mobile phase. Alternatively, the pump 20 might be comprised of plural individual pumping units, with plural of the pumping units each receiving and pumping a different solvent or mixture, so that the mixing of the mobile phase (as received by the separating device 30) occurs at high pressure and downstream of the pump 20 (or as part thereof). The composition (mixture) of the mobile phase may be kept constant over time, the so called isocratic mode, or varied over time, the so called gradient mode.

A data processing unit 70, which can be a conventional PC or workstation comprising one or more of the processing devices alluded to above, might be coupled (as indicated by the dotted arrows) to one or more of the devices in the fluid separation system 10 in order to receive information and/or control operation. For example, the data processing unit 70 might control operation of the pump 20 (e.g. setting control parameters) and receive therefrom information regarding the actual working conditions (such as output pressure, flow rate, etc. at an outlet of the pump). The data processing unit 70 might also control operation of the solvent supply 25 (e.g. setting the solvent's or solvent mixture to be supplied) and/or the degasser 27 (e.g. setting control parameters such as vacuum level) and might receive therefrom information regarding the actual working conditions (such as solvent composition supplied over time, flow rate, vacuum level, etc.). The data processing unit 70 might further control operation of the sampling unit 40 (e.g. controlling sample injection or synchronization sample injection with operating conditions of the pump 20). A switchable valve (not shown) can be operated so as to adjust a desired fluidic coupling within the fluid separation system 10. The separating device 30 might also be controlled by the data processing unit 70 (e.g. selecting a specific flow path or column, setting operation temperature, etc.), and send—in return—information (e.g. operating conditions) to the data processing unit 70. Accordingly, the detector 50 might be controlled by the data processing unit 70 (e.g. with respect to spectral or wavelength settings, setting time constants, start/stop data acquisition), and send information (e.g. about the detected sample compounds) to the data processing unit 70. The data processing unit 70 might also control operation of the fractionating unit 60 (e.g. in conjunction with data received from the detector 50) and provides data back.

In the following, referring to FIG. 2, a sample injector for use in a fluid separation system 10 as described in FIG. 1 for separating components of a fluidic sample in a mobile phase according to an exemplary embodiment of the invention will be explained.

The sample injector comprises a switchable valve 90, a sample loop 230 in fluid communication with the switchable valve 90 and contributing to aspirating the fluidic sample from a fluid container 214 (for example, a vial), and a metering pump 270 in fluid communication with the sample loop 230 and configured for introducing a metered amount of the fluidic sample into needle 202.

The switchable valve 90 comprises two valve members which are rotatable with respect to one another. By rotating these two valve members along a rotation axis which is perpendicular to the paper plane of FIG. 2, a plurality of ports 262 formed in one of the valve members and a plurality of oblong arcuate grooves 264 formed in the other one of the valve members can be selectively brought in or out of fluid communication with one another. Since the various ports 262 are connected to dedicated ones of fluidic channels of the fluidic system as shown in FIG. 2, automatically switching the switchable valve 90 may allow to operate the fluid separation system 10 in different fluid communication configurations. The switchable valve 90 is configured as a six port high pressure valve in the embodiment of FIG. 2.

Fluid communication between the pump 20, which may be a high pressure pump, and the separating device 30 can be accomplished by an according switching state of the switchable valve 90. In such a fluidic path, a high pressure of for instance 100 MPa may be present which may be generated by the pump 20. In contrast to this, the pressure state in the sample loop 230 may be for instance smaller than 0.1 MPa when introducing a sample into the sample loop 230. When this sample loaded on sample loop 230 is to be loaded on separating device 30, the pressure in sample loop 230 is also high, for instance 100 MPa.

For the purpose of loading the sample, a needle 202 may be driven out of a correspondingly shaped seat 200 so that the needle 202 can be immersed into fluid container 214 accommodating a fluidic sample to be loaded onto the needle 202.

Figure 2:
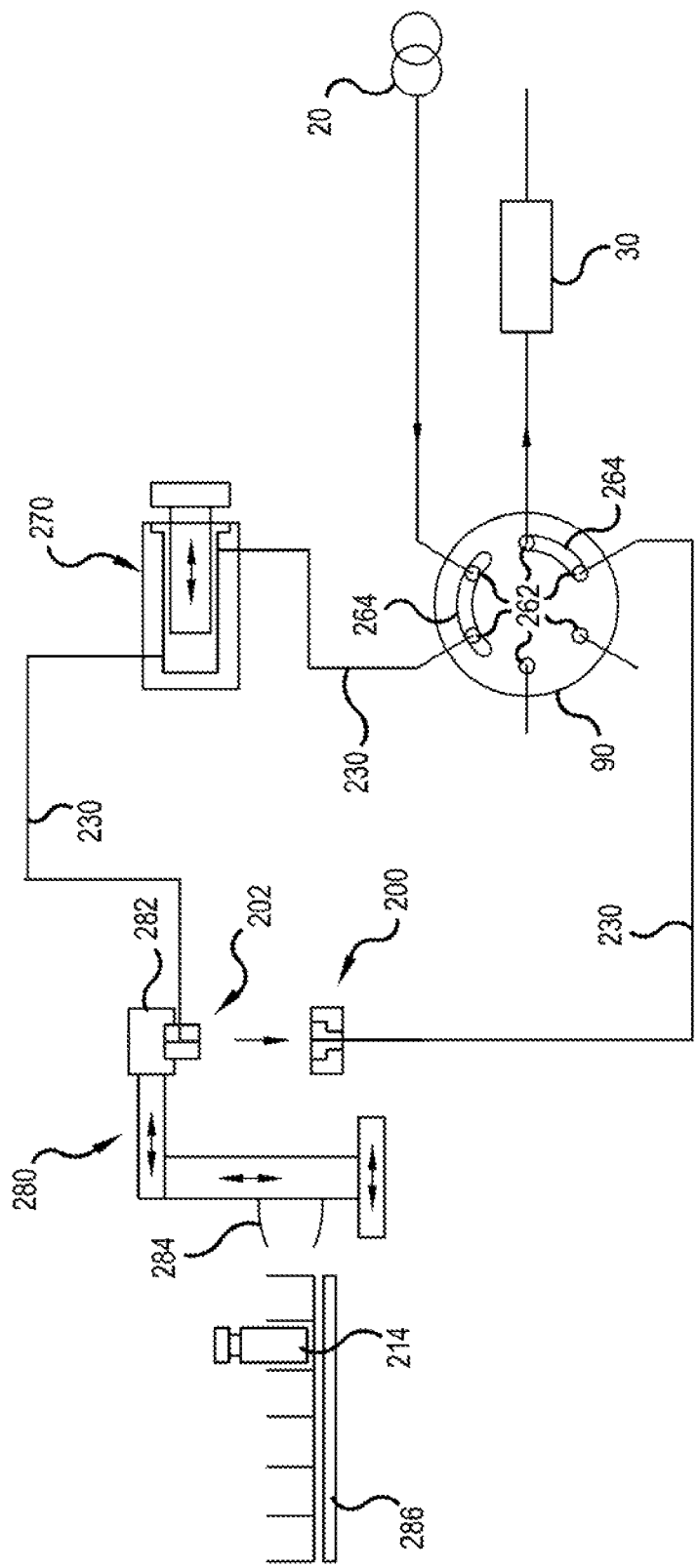
FIG. 2 to FIG. 4 show a sample injector of a liquid separation device in accordance with embodiments of the present invention in three different operation modes.

Hence, FIG. 2 shows the movable needle 202 which can be moved under control of a control unit (not shown, for instance a central processing unit or microprocessor), between fluid container 214 and seat 200.

Hence, when the needle body with its conically tapering tip is immersed into the fluid container 214, it is possible to suck a fluidic sample accommodated within fluid container 214 into the fluidic conduit in the needle body as well as into fluid connected conduits.

Subsequently, the sample may be loaded onto the separating device 30. However, for this purpose, it is required that the needle 202 be inserted into the seat 200. As can be taken from the schematic drawing in FIG. 2, also the seat 200 has a central bore which allows for fluid communication between the fluidic conduit of the needle 202 and the fluidic conduit of the seat 200. Therefore, the sample which has been previously loaded via the conduit of the needle body can be conducted through the conduits and finally onto the separating device 30.

Furthermore, FIG. 2 illustrates that the sample injector includes a robot arm 280 which is configured for moving the injection needle 202. FIG. 2 shows the sample injector in an operation mode in which the injection needle 202 is connected to the robot arm 280. The robot arm 280 is connected to or comprises, or both, one or more processing devices (not shown) that were alluded to above. In operational mode, the robot arm 280 is configured to move the injection needle 202 between the fluid container 214 containing the fluid on the one hand and the seat 200 on the other hand. In FIG. 2, the robot arm 280 presently moves in such a direction so as to insert the needle 202 into the seat 200 for subsequently injecting a fluid which has previously been aspirated by the injection needle 202 into the fluidic path between pump 20 and separating device 30. In this configuration of FIG. 2, the injection needle 202 is mounted temporarily on a needle mounting unit 282 of the robot arm 280.

Figure 3:
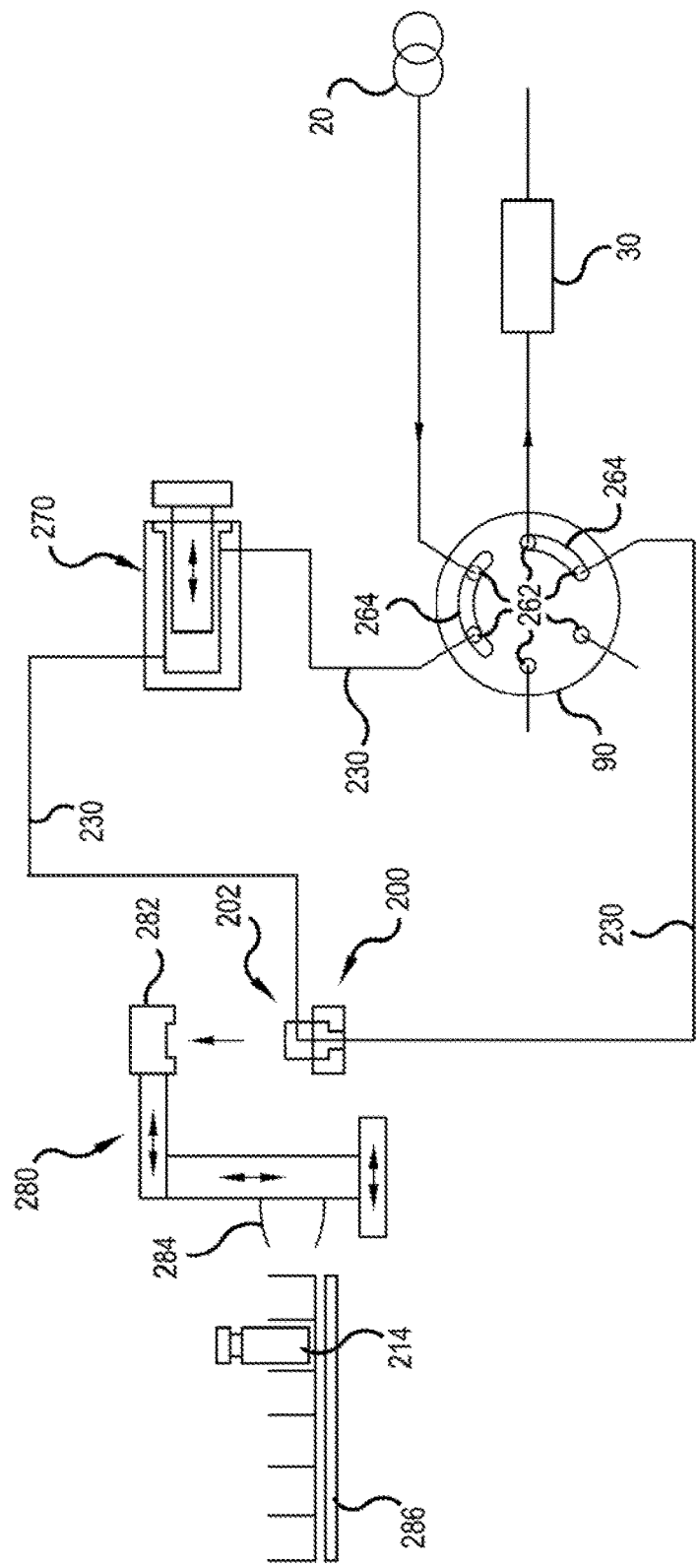

After having completed the downward motion of the robot arm 280 (together with mounted needle 202) and the needle 202 has been inserted into the seat 200, the needle 202 is selectively disconnected from the needle mounting unit 282 and therefore from the robot arm 280 so that the injection needle 202 remains accommodated in the seat 200 and is now separate from the robot arm 280, compare FIG. 3.

In the scenario of FIG. 3, the switchable valve 90 can be switched so that the fluid which has previously been injected in the needle 202 is transferred into a fluidic path between the pump 20 and the separating device 30. During the time interval in which this injection procedure is carried out, the robot arm 280 is free to be used for any other task.

Figure 4:
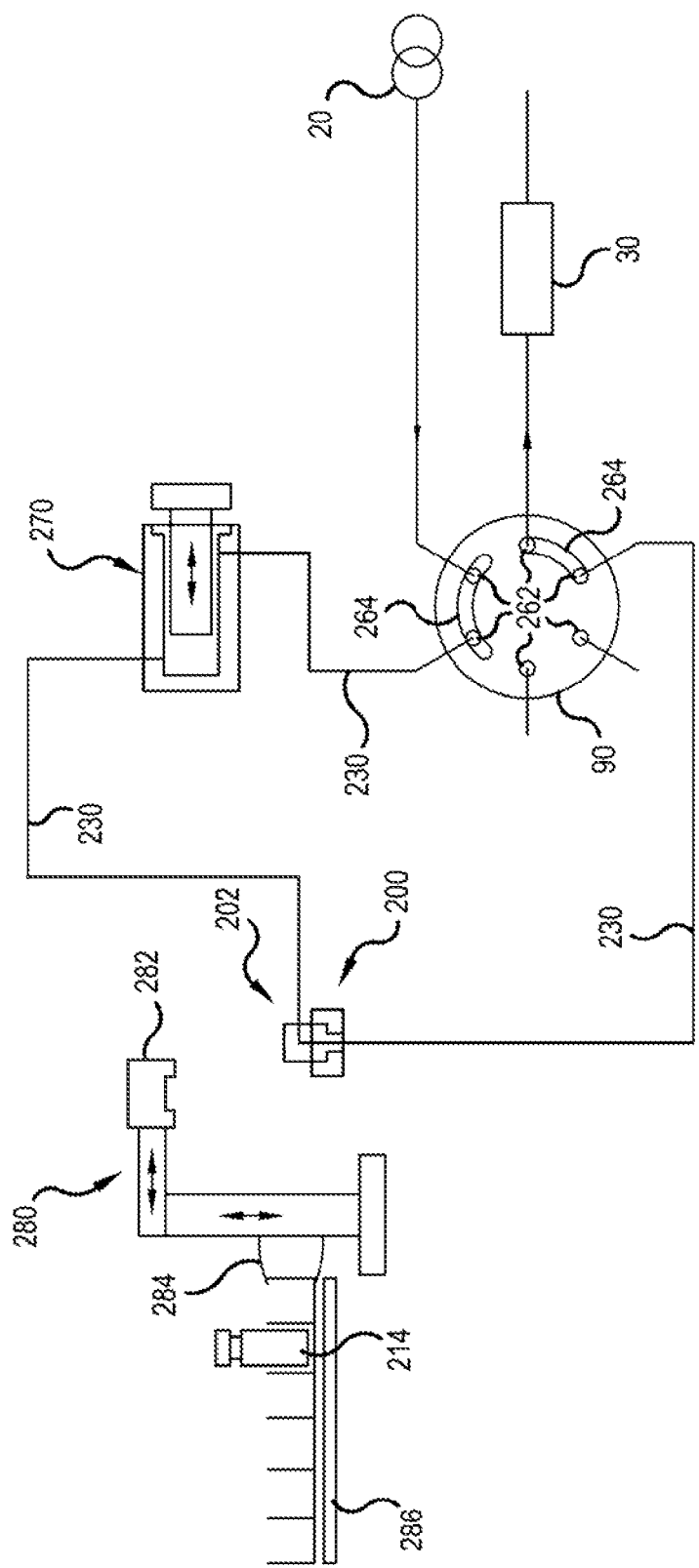

For instance, as shown in FIG. 4, the robot arm 280, now being disconnected from the needle 202, can be moved towards the fluid container 214 so that a fluid container gripping unit 284 (illustrated in FIG. 2 to FIG. 4 as some kind of clamping mechanism) is capable to grip the fluid container 214 for handling it. For instance, the fluid container 214 may be placed on a specific fluid container support 286 so as to be located at a defined position so that the needle 202 can be moved towards the fluid container 214 for aspirating the fluid (the latter operation mode is not shown in the figures).

In the following, referring to FIG. 5 and FIG. 6, a sample injector 500 for injecting a fluid into a fluidic path according to an exemplary embodiment will be explained.

The sample injector 500 comprises a robot arm 502 which is configured for moving an injection needle 506. The latter may be attached to an injection needle holder 504 of the robot arm 502 for a moving operation. Such a moving operation of an injection needle 506 which in the operation mode shown in FIG. 5 and FIG. 6 is presently disconnected from the robot arm 502, can be performed between a fluid container containing a fluid to be aspirated into the injection needle 506 on the one hand and a seat 508 in fluid communication with the fluidic path (into which the fluid is to be subsequently injected) on the other hand.

Figure 5:
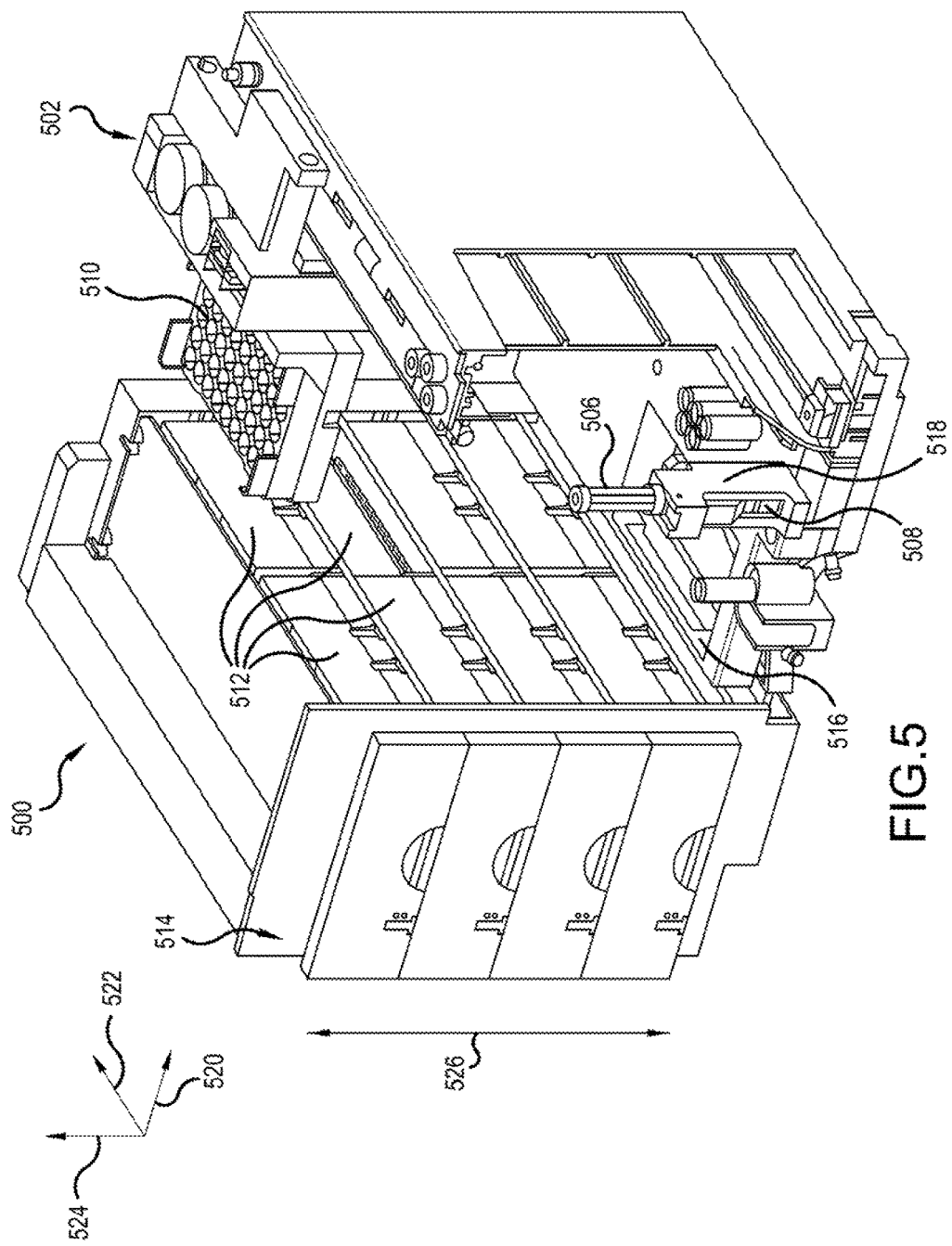
FIG. 5 is a first view of a sample injector system according to an exemplary embodiment of the invention showing a robot arm and a fluid container rack.
Figure 6:
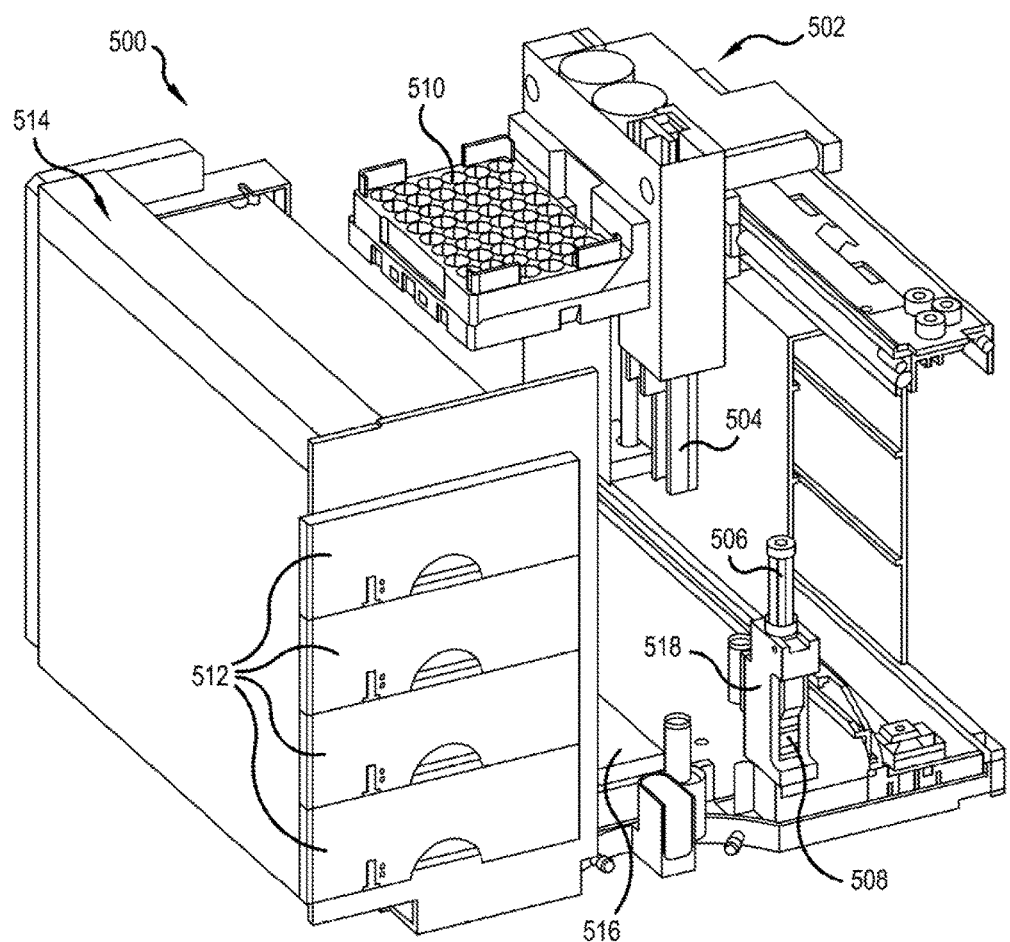
FIG. 6 shows a second view of the sample injector of FIG. 5.

Such a motion of the needle 506 held by the robot arm 502 can be better seen from the illustrations of a robot arm 502 of a sample injector 500 in FIG. 7 to FIG. 10 (the sample injector 500 of FIG. 5 to FIG. 6 is very similar to the one of FIG. 7 to FIG. 10).

Figure 8:
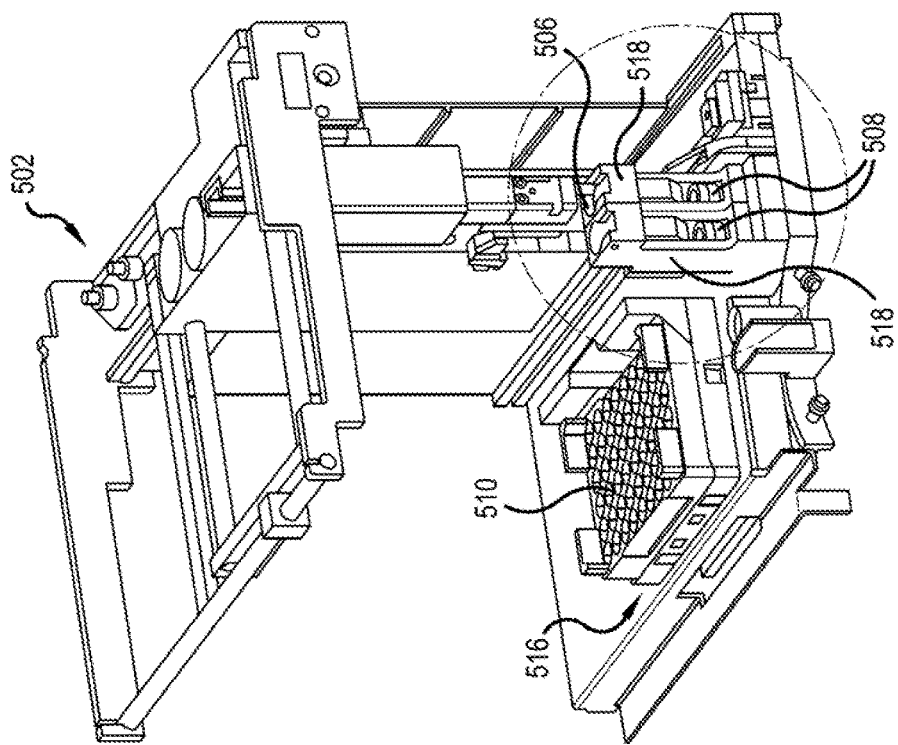
FIG. 7 and FIG. 8 show two different views of a robot arm serving a well plate together with two needle park stations of a sample injector according to an exemplary embodiment of the invention.
Figure 7:
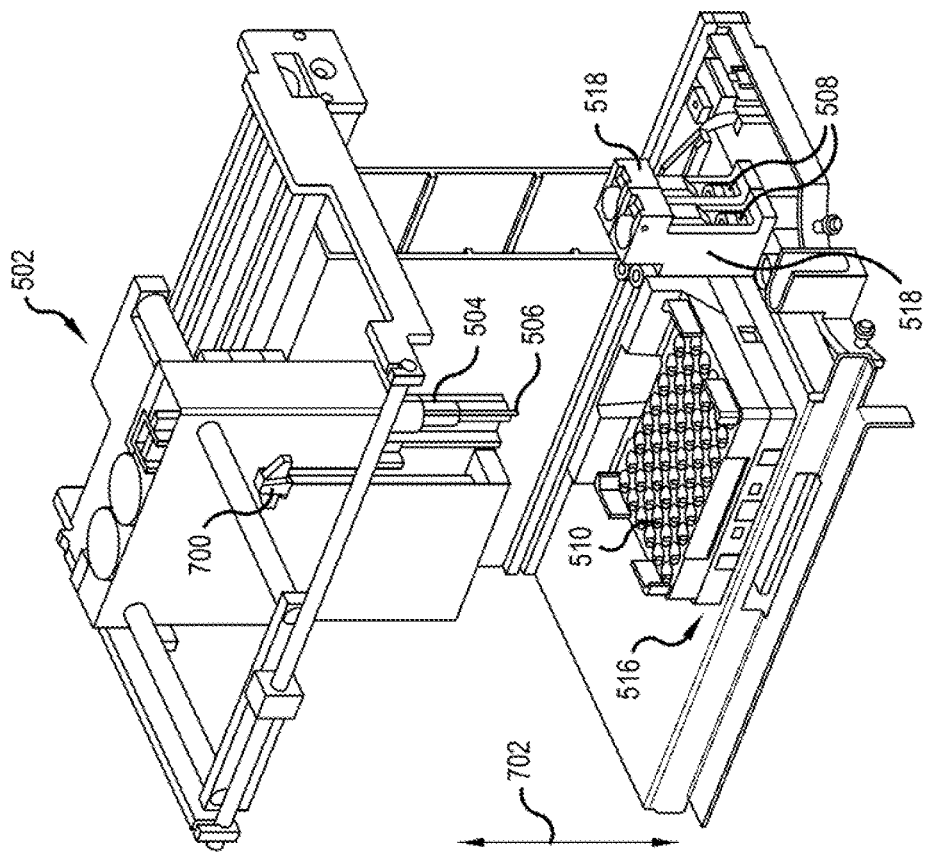
Figure 9:
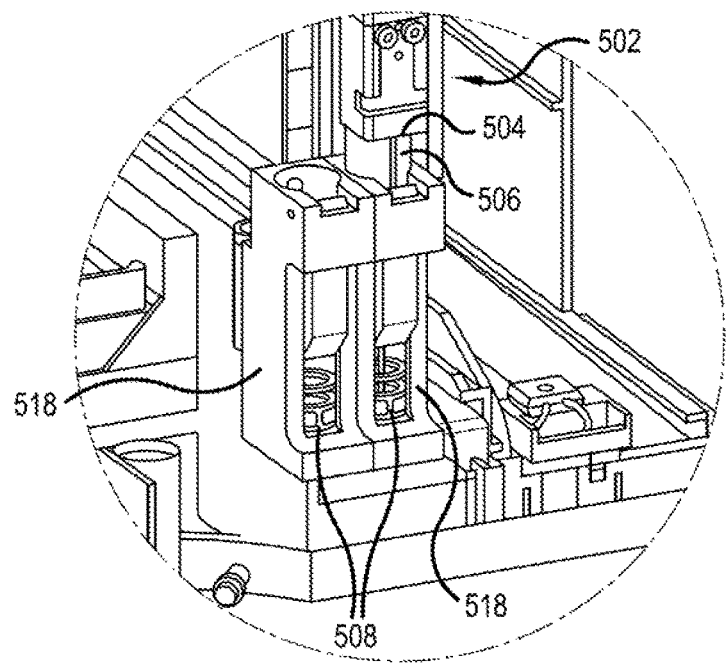
FIG. 9 shows a detail of the sample injector of FIG. 8 illustrating the needle park station in cooperation with the robot arm.
Figure 10:
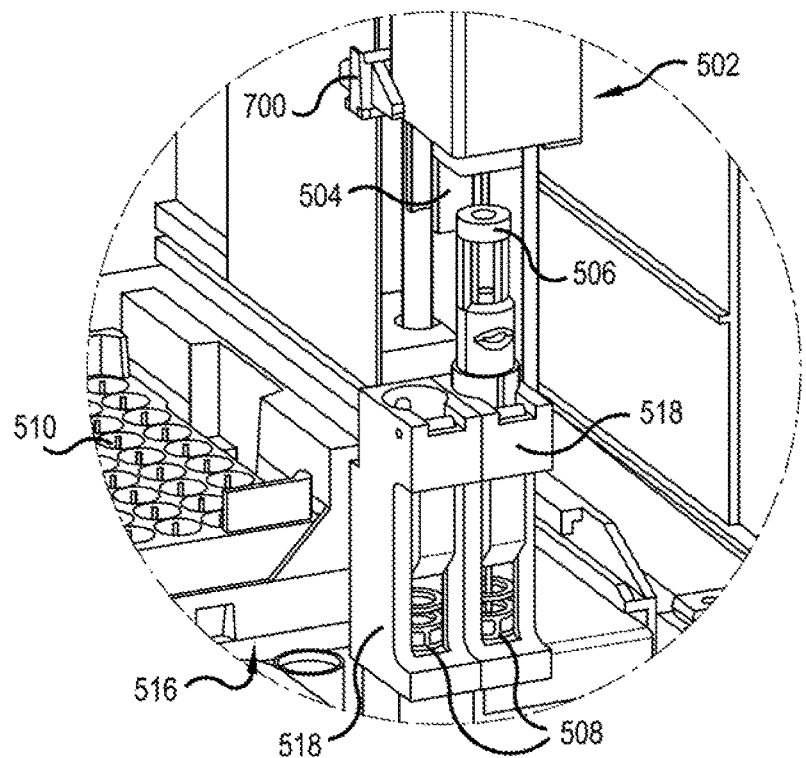
FIG. 10 shows another detailed view of the needle park station of the sample injector of FIG. 8 in an operation mode in which the needle is disconnected from the robot arm.

FIG. 7 shows needle 506 attached to the robot arm 502 so that needle park stations 518 and seats 508 are empty. FIG. 8 shows how the needle 506 is disconnected from the robot arm 502 and inserted in one of the needle park stations 518. FIG. 9 shows a detail of the scenario of FIG. 8. FIG. 10 shows a scenario similar to FIG. 9 in which the needle 506 is disconnected from the robot arm 502.

Figure 13:
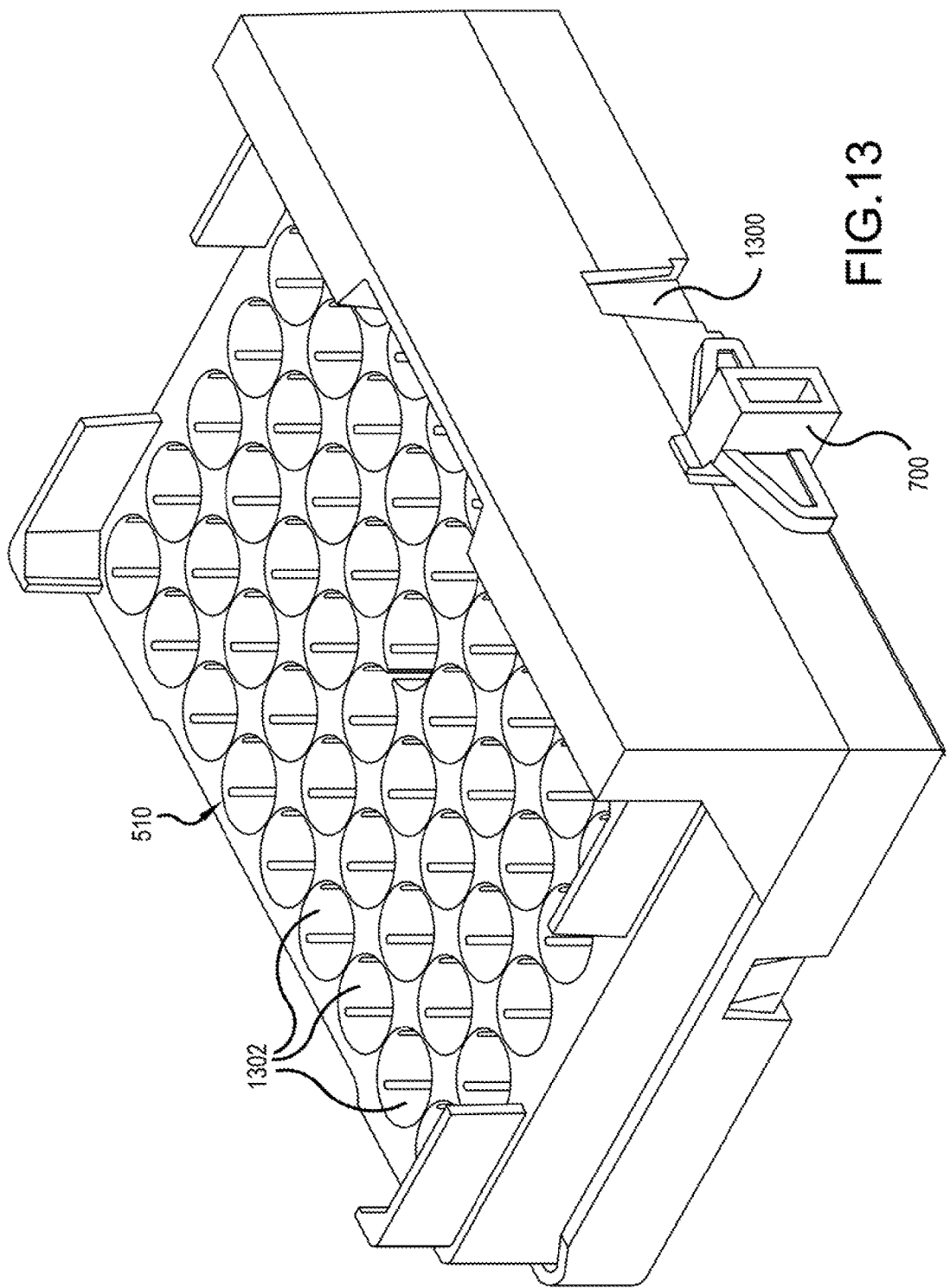
FIG. 13 illustrates a well plate as an example for a fluid container having a coupling for a robot arm according to an exemplary embodiment of the invention.

FIG. 7 shows a well plate 510 having a plurality of fluid containing recesses (also denoted as wells) each configured for receiving a corresponding fluid (such as a biological sample, a solvent, etc.). In the operation modes of FIG. 5 and FIG. 6, the sample plate 510 is handled by the robot arm 502, i.e. a well plate holder of the robot arm 502 is presently connected to the sample plate 510 (or well plate). The well plate holder can be brought in engagement with a correspondingly configured connection piece 1300 of the sample plate 510, which can be best seen in FIG. 13, located at a lateral surface of the sample plate 510.

Thus, the robot arm 502 can be used in a first operation mode in which it takes a sample plate 510 (such as a microtiter plate) out of one of a plurality of sample plates which are presently accommodated in a horizontally and vertically stacked manner in different compartments 512 of a fluid container rack 514 which can be best seen in FIG. 5. The well plate rack 514 is operable with a push loading drawer mechanism. In other words, the robot arm 502 may be moved along three perpendicular directions to access any desired position in a three-dimensional space, i.e. has a mechanism to move along two horizontal directions 520, 522 and one vertical direction 524, so as to able to take a selected one of the well plates 510 out of a corresponding well plate compartment 512 of the fluid container rack 514 and to place it on a correspondingly dimensioned and located well plate support 516, i.e. a specifically defined surface area of the sample injector 500 on which the well plate 510 may be placed by the robot arm 502 for further operation.

When the well plate 510 is placed on the well plate support 516, the robot arm 502 may disconnect from the previously moved well plate 510. After this, the robot arm 502 may then move to a needle 506 which is presently parked in a seat 508 and at a needle park station 518 (compare FIG. 5 or FIG. 10). The robot arm 502 may then take up such a needle 506 by attaching or connecting it to the injection needle holder 504. Subsequently, the robot arm 502 may take along the needle 506 and may move it to the well plate support 516 so that the needle 506 may be immersed into fluid of a corresponding well of the well plate 510 for aspirating such a fluid, i.e. for sucking such a fluid into a capillary of the needle 506. It is also possible that taking up the needle 506 by the robot arm 502 connects the needle 506 fluidicly to a capillary carried along with the robot arm 502. The fluid volume to be aspirated may be defined by a metering device (such as the one shown in FIG. 2 to FIG. 4) being in fluid communication with the connected capillary. After having aspirated the fluid, the needle 506 being still connected to the injection needle holder 504 of the robot arm 502 may be then moved back into the seat 508 so as to be brought in fluid-tight connection with the seat 508. This procedure may be supported by foreseeing the seat 508 with assigned needle park station 518.

Hence, the robot arm 502 may be operable to contribute to the fluid aspiration of the needle 506 and to its subsequent spatial transfer to the seat 508 for fluid injection while the well plates 510 remain spatially fixed. However, the robot arm 502 may also be operable to contribute to the handling of the well plates 510 between the fluid container rack 514 and the well plate support 516. Since these two tasks are required alternatively (i.e. one task is needed while the other one is not needed, and vice versa), the resources of the robot arm 502 can be used very efficiently basically without inactive time intervals.

In the embodiment of FIG. 5 and FIG. 6, a single seat 508 with a single assigned needle park station 518 is shown, whereas in the embodiment of FIG. 7 to FIG. 10, two seats 508 and two assigned needle park stations 518 are provided. A skilled person will understand that any desired other number of seats 508/needle park stations 518 may be foreseen so that the robot arm 502 can serve also multiple seats 508, multiple injection needles 506 and multiple needle park stations 518, while simultaneously being capable of serving multiple well plates 510 being stored in the well plate compartments 512 of the well plate rack 514.

After having taken a dedicated well plate 510 from a corresponding well plate compartment 512 of the well plate rack 514 by the robot arm 502 using the well plate holder, the robot arm 502 may move the taken well plate 510 to the well plate support 516. Thereafter the robot arm may move to connect to a needle 506 (which may be presently stored in a corresponding seat 508 and fastened by a needle park station 518) via the injection needle holder 504. Then, the robot arm 502 having the connected (but disconnectable) injection needle 506 at the injection needle holder 504 may move to a dedicated well (shown with reference numeral 1302 in FIG. 13) which is filled with a fluid such as a sample or a solvent. The injection needle 506 may then aspire such a fluid from a corresponding well 1302 of the well plate 510. The so aspired fluid may then be injected into a selectable seat 508, or more precisely into a fluid conduit connected thereto for injecting the sample or solvent into a fluidic path between a pump 20 and a separating device 30, as shown in FIG. 1. For this purpose, the robot arm 502 moves the injection needle 506 connected to the injection needle holder 504 towards the corresponding seat 508/needle park station 518. Upon vertically lowering the injection needle 506 connected to the injection needle holder 502 by a downward motion of the robot arm 502, the injection needle 506 will insert into a reception hole of the needle park station 518, will therefore be brought in fluid-tight engagement with the seat 508 and will be automatically disconnected from the injection needle holder 504 and connected to a corresponding supporting element of the needle park station 518.

Hence, the injection needle 506 is configured for aspirating the fluid from the fluid container 510, when the injection needle 506 has been moved to the fluid container 510, and is configured for injecting aspirated fluid into the fluidic path when the injection needle 506 is accommodated in the seat 508. The seat 508 is configured for accommodating the injection needle 506 and for providing fluid communication with the fluidic path. The robot arm 502 in turn is configured for selectively disconnecting the injection needle 506 from the robot arm 502 when the injection needle 506 is accommodated in the seat 508. While the injection needle 506 remains accommodated in the seat 508 held by the needle park station 518, the robot arm 502 is free for performing a further task while the injection needle 506 remains disconnected from the robot arm 502. This further task may for instance be the well plate handling mentioned above in which the robot arm 502 handles a well plate 510, i.e. takes a certain well plate 510 out of a corresponding well plate compartment 512 of the well plate rack 514, and places the well plate 510 on the well plate support 516. R is also possible that the robot arm 502, in this time interval, puts back a well plate 510 which is presently located on the well plate support 516 into the corresponding compartment 512 of the well plate rack 514.

In the embodiment of FIG. 7, FIG. 8, FIG. 9, and FIG. 10, in which multiple seats 508/needle park stations 518 and multiple needles 506 are present, the robot arm 502 may also serve another needle 506, another seat 508 and/or another needle park station 518 while the fluid which has been aspirated into a needle 506 is presently injected via the seat 508 into one of fluidic paths.

When the injection needle 506 is accommodated in the seat 508, there is a fluid-tight connection or a pressure-tight connection between the injection needle 506 and the seat 508 so that the aspirated fluid may be injected into the fluidic path without leakage.

The needle park station 518 retains the injection needle 506 while the injection needle 506 remains accommodated in the seat 508. An advantageous feature of the sample injector 500 is also that the robot arm 502, the injection needle 506, the seat 508 and the needle park station 518 cooperate for sealing the fluid conduit of the injection needle 508 with regard to an environment upon disconnecting the injection needle 506 from the robot arm 502. In other words, when the robot arm 502 moves upwardly after having inserted the still connected injection needle 506 into the seat 508 and to the needle park station 518, a subsequent upward motion of the robot arm 502 will not only detach the injection needle 506 from the injection needle holder 504 of the robot arm 502 which is then free for serving other tasks, but at the same time an upper end of the injection needle 506 will be sealed so that the aspirated fluid may be injected in a downward direction into the seat 508 by a sucking operation. Furthermore, when the needle 506 is parked in the needle park station 518 and is in fluid-tight connection with the seat 508, the robot arm 502 will simply move downwardly again and will operate a locking mechanism so as to unlock the needle 506 from the needle park station 518 and the seat 508, and will simultaneously connect to the injection needle 506 by the injection needle holder 504.

As can be further taken from FIG. 5, the robot arm 502 may be moved along first horizontal direction 520, second horizontal direction 522 (perpendicular to first horizontal direction 520) and third vertical direction 524. In the vertical direction 524, the robot arm 502 has two separately and independently operable lift mechanisms. A first lift mechanism is configured for handling the well plates 510, i.e. for taking out a dedicated well plate 510 from a corresponding well plate compartment 512 of the well plate rack 514 to the well plate support 516 and/or for putting it back from the well plate support 516 to a corresponding well plate compartment 512 of the well plate rack 514. Therefore, the first lift mechanism of the robot arm needs to be capable of operating over a first stroke length which is indicated schematically in FIG. 5 with reference numeral 526 and which may basically correspond to the height of the well plate rack 514. On the other hand, the robot arm 502 has a second lift mechanism configured for handling the injection needle 506 over a second stroke length along the vertical lift axis 524. Thus, for operating the needle 506 between a first operation mode in which it is immersed in a well 1302 of the well plate 510 and a second operation mode in which it is placed in the seat 508, the needle 506 may also be lifted for being moved along the arrangement, as can best be seen in FIG. 7. A corresponding second stroke length is indicated schematically with reference numeral 702. As can be taken from a comparison of FIG. 5 and FIG. 7, the first stroke length 526 is larger than the second stroke length 702. The robot arm 502 is hence configured so as to be capable of operating the well plate holder along the first stroke length 526 and the injection needle holder 504 along the second stroke length 702.

Figure 11:
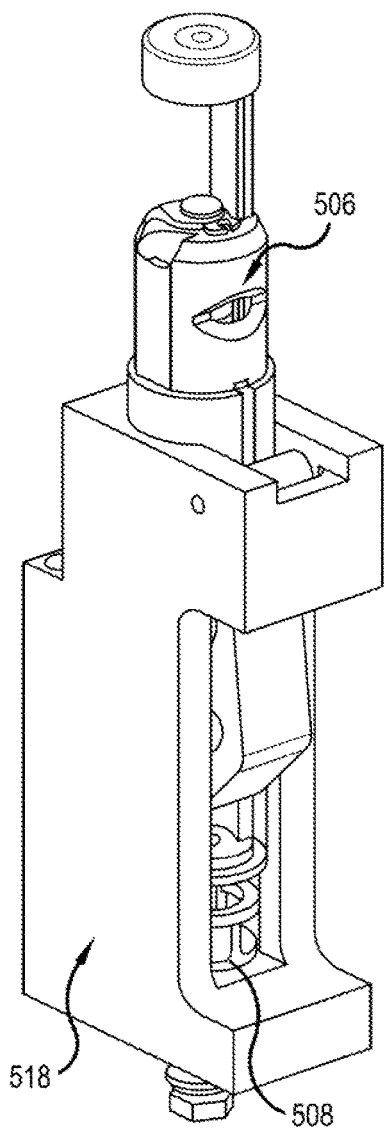
FIG. 11 and FIG. 12 are two different images illustrating a needle park station of a sample injector with a connected needle according to an exemplary embodiment of the invention in a three dimensional view and in a cross-sectional view.

FIG. 11 shows a three-dimensional view of a needle park station 518 together with a corresponding seat 508 and a cartridge-type injection needle 506 which has presently been disconnected from the robot arm 502, more precisely from the injection needle holder 504 of the robot arm 502.

Figure 12:
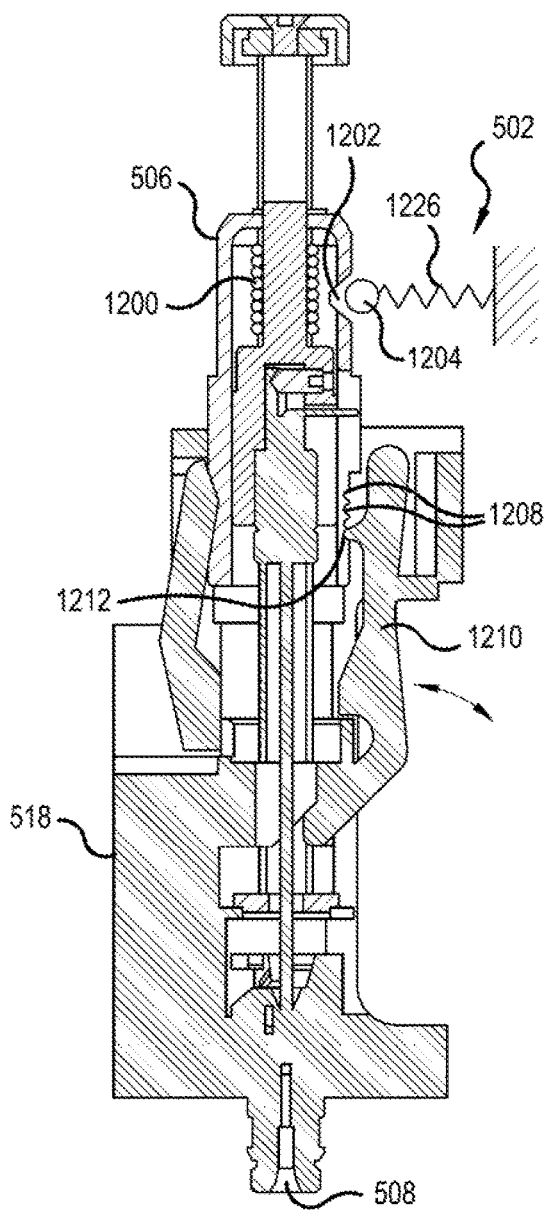

FIG. 12 shows a cross-sectional view corresponding to FIG. 11 and will be described in more detail in the following in terms of the combined locking-unlocking mechanism involved in the transfer of the needle 506. The robot arm 502 (only a part thereof is shown schematically in FIG. 12), the seat 508 and the needle park station 518 now cooperate so that upon inserting the injection needle 506 into the seat 508 by the robot arm 502, a biasing spring 1200 of the injection needle 506 is biased to as to exert a sealing force between the injection needle 506 and the seat 508. Additionally, a mutual locking mechanism of the injection needle 506 and the needle park station 518 is activated. For this purpose, the robot arm 502 and the injection needle 506 comprise cooperating first retaining elements configured for retaining the injection needle 506 at the robot arm 502 with a first retaining force while the injection needle 506 is outside the seat 508. These first retaining elements can be realized by a latching recess 1202 of the injection needle 506 and a corresponding latching ball (or other protrusion) 1204 configured for engaging the latching recess 1202. A further biasing spring 1226 of the robot arm 502 may press the latching ball 1204 into the latching recess 1202 for exerting the first retaining force.

Furthermore, the needle park station 518 and the injection needle 506 comprise cooperating second retaining elements configured for retaining the injection needle 506 at the needle park station 518 with the second retaining force being larger than the first retaining force and being operable when the injection needle 506 is inserted into the seat 508 so that subsequently retracting the robot arm 502 from the seat 508 releases the injection needle 506 from the robot arm 502 and retains the injection needle 506 at the needle park station 518. These second retaining elements can be realized by further latching recesses 1208 of the injection needle 506 and a pivotable retaining lever 1210 which can be pivoted in a way as indicated by an arrow in FIG. 12 and which has a protrusion 1212 for engaging one of the one or more latching recesses 1208. Thus, the mutual locking mechanism is provided by the second retaining elements 1208, 1210, 1212. Apart from this, a latch may be provided which may be actuated by the robot arm 502 to disengage the second retaining elements 1208, 1210, 1212 from one another so that subsequently retracting the robot arm 502 pulls the injection needle 506 along with the robot arm 508.

Therefore, the described mechanism results in the fact that when the injection needle 506 is still connected to an injection needle holder 504 of the robot arm 502 and will be placed in the seat 508, it will be disconnected from the injection needle holder 504 upon retracting the robot arm 502 upwardly. At the same time, the injection needle 506 will be locked to the needle park station 518 so as to provide for a secure connection between seat 508 and needle 506. Furthermore, an upper end portion of the needle 506 is sealed so that aspirated fluid in the capillary of the needle 506 can subsequently be injected into the fluidic path connected to the seat 508.

Figure 14:
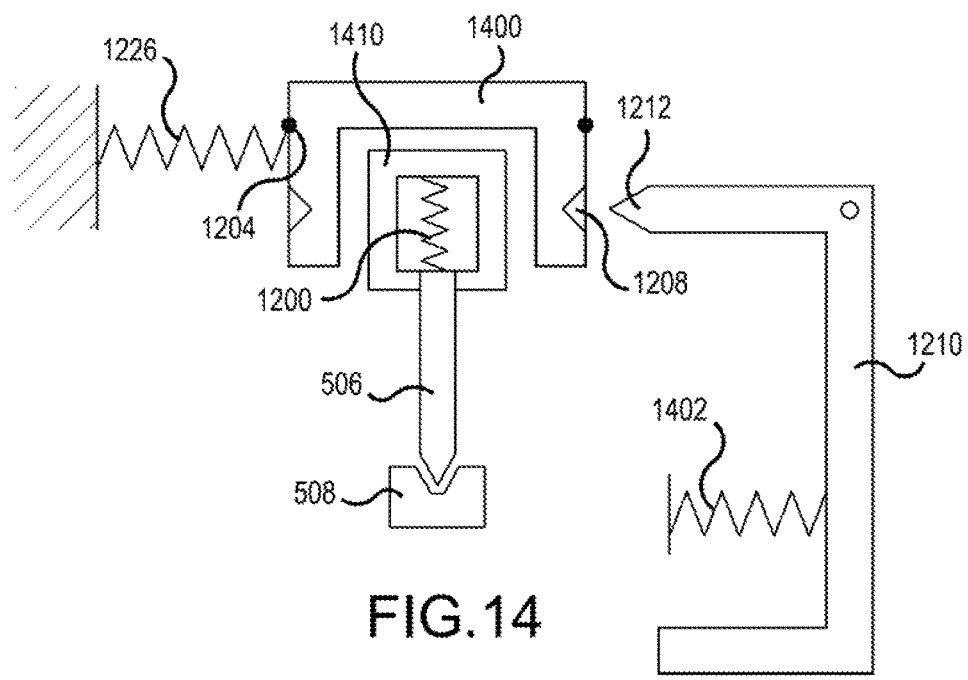
FIG. 14 is a schematic view showing a mechanism of operating a needle cartridge by a robot arm together with a needle park station.

FIG. 14 is a schematic illustration of the combined locking and unlocking mechanism described referring to FIG. 12 and specifically shows that the injection needle 506 is arranged within a package denoted schematically with reference numerals 1400, 1410. Furthermore, FIG. 14 shows that an additional spring 1402 can be provided for biasing the lever 1210 so that the protrusion 1212 will be forced into the recess 1208.

Figure 15:
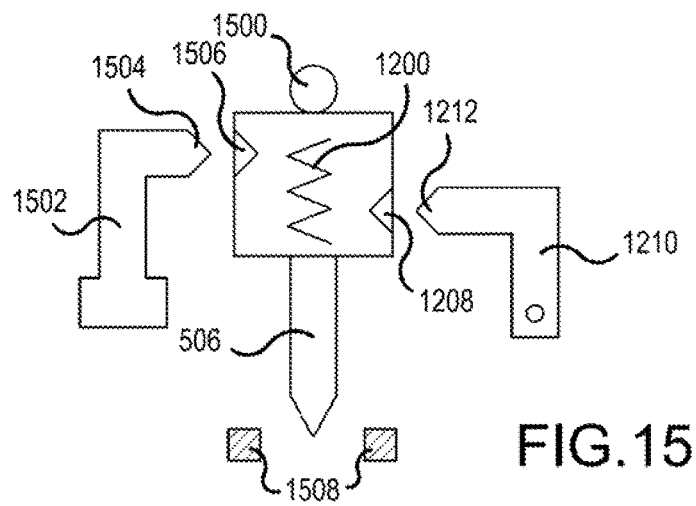
FIG. 15 schematically illustrates an example as to how a disconnection of an injection needle can be performed.

FIG. 15 shows a part of the schematic arrangement of FIG. 14 and additionally shows a shaft or actuator 1500 of the injection needle 506. Furthermore, as compared to the ball 1204 and the spring 1226, the connection between robot arm 502 and the injection needle 506 may in this embodiment be realized by a lever 1502 having a protrusion 1504 cooperating with a recess 1506 in the package of the needle 506.

As can furthermore be taken from FIG. 15 schematically, the robot arm 502 may comprise a stripper tool 1508 configured for stripping off a fluid container (not shown in FIG. 15) from the injection needle 506 after having aspirated the fluid from the fluid container. Such a stripper tool 1508 may be advantageous when the needle 506 penetrates a septum or a membrane of a vial (for a sterile storage of the fluid), so that after having aspirated fluid from the vial, it may happen that the injection needle 506 may remain connected to the vial. The stripper tool 1508 will then allow the needle 506 to be retracted from the vial.

Figure 16:
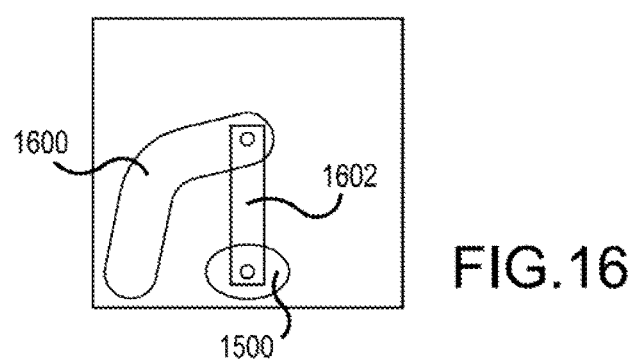
FIG. 16 schematically illustrates a force reduction principle for reducing a handling force exerted by a robot arm for operating a disconnectable needle.

FIG. 16 schematically shows how the shaft 1500 (such as a camshaft) can cooperate with a curved recess 1600 via a force transmission lever 1602. By taking this measure, the injection needle 506 having the lever mechanism shown in FIG. 16 is operable by the robot arm 502 with a reduced force exerted by the robot arm 502 required for sealing the fluid conduit by lever action.

More generally, a force required to be exerted by the robot or robot arm for sealing the needle may be reduced by implementing a force transmission which may use a guide rail, thereby benefiting from a lever action effect.

In the following, referring to FIG. 17 to FIG. 22, a sample injector 500 being very similar to the above-described sample injectors 500 according to an exemplary embodiment of the invention will be explained.

Generally, the sample injector 500 provides for a combined plate handler and sample injection robot. The autosampler 500 shown in FIG. 17 has the advantage to increase sample capacity to more than 400 vials or eight or more well plates. Furthermore, it is possible to handle vials but also well plates with the sample injector 500. Additionally, the sample injector 500 has a very low internal volume to allow fast analysis.

In a concept, where the sample needs to be transported to the sampling unit, it would be difficult to handle well plates. In another concept, where the needle moves to the sample, a long connection capillary is required due to the increased amount of sample plates which has to be addressed. The plate handler or sample injector 500 of FIG. 17 combines the advantages of both systems. It contains a coupling device for pallets. With this coupling mechanism, pallets containing the sample trays can be transported from/to a hotel system (fluid container rack 514) to a parking station (fluid container support 516) inside the autosampler 500. The hotel system contains a plurality of pallets with random access. The plate handler also contains a holding mechanism for the injection needle 506. When a pallet with the sample tray is placed on the parking station, the robot (which is also denoted as robot arm 502) moves a needle 506 to the according sample for sample aspiration.

An advantage of such a combined plate/needle movement system is that only one x, y, z robot system is needed for the plate and for the needle movement. The injection needle only has to be moved in the area of one plate (plate on park station). Thus, a short connection capillary between a needle and sampling unit can be achieved. With the x, y movement of only one well plate, the robot is available to reach two stacks of pallets with its coupling mechanism. Thus, in the described embodiment, a sample capacity of 2 stacks each having 6 sample trays can be accessed. Since the sampling needle is movable, the needle can be cleaned in a needle wash port, if desired or required.

Figure 17:
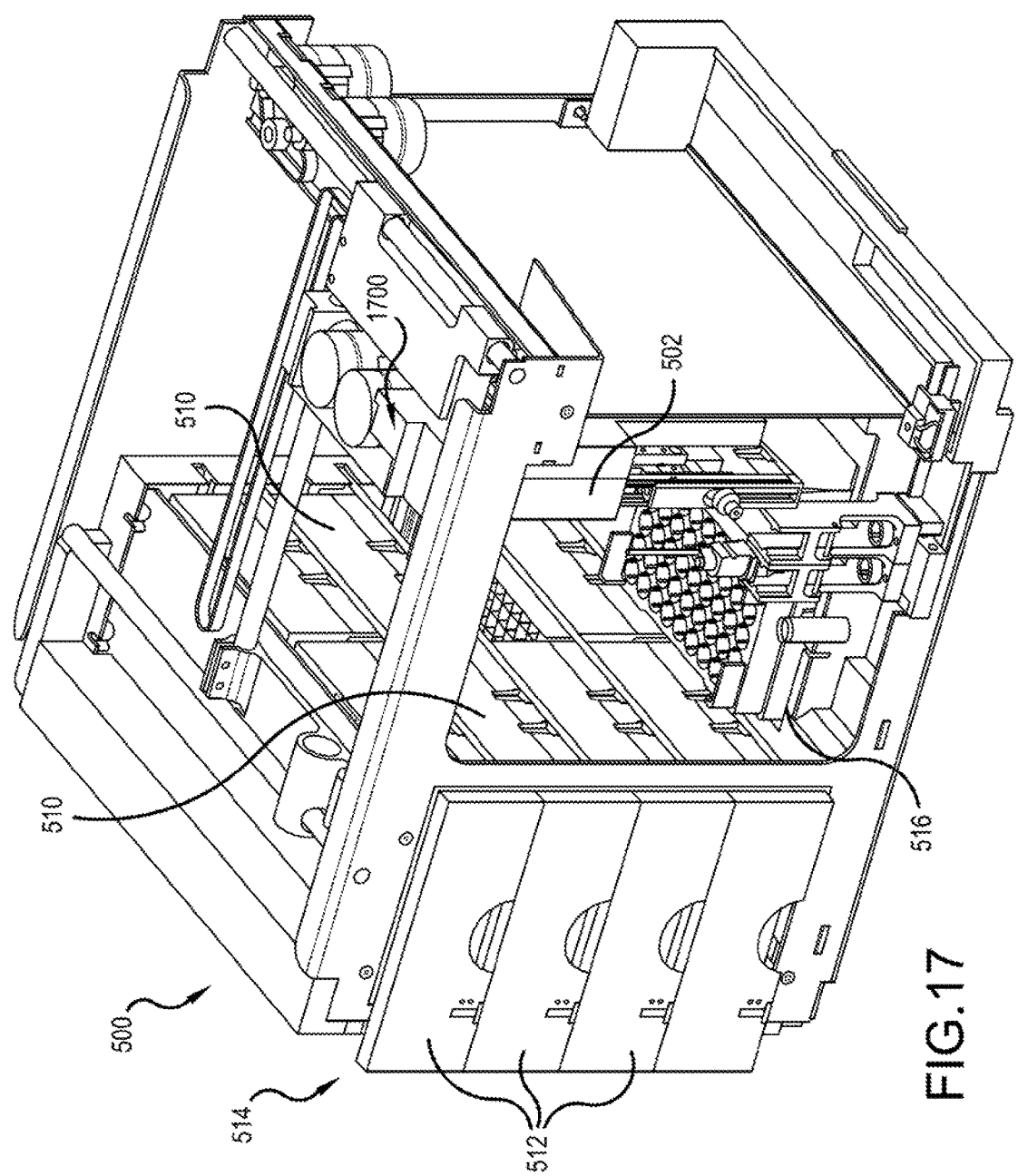
FIG. 17 shows a three-dimensional view of a sample injector according to an exemplary embodiment of the invention.

The x, y, z robot is denoted with reference numeral 1700 in FIG. 17.

Figure 19:
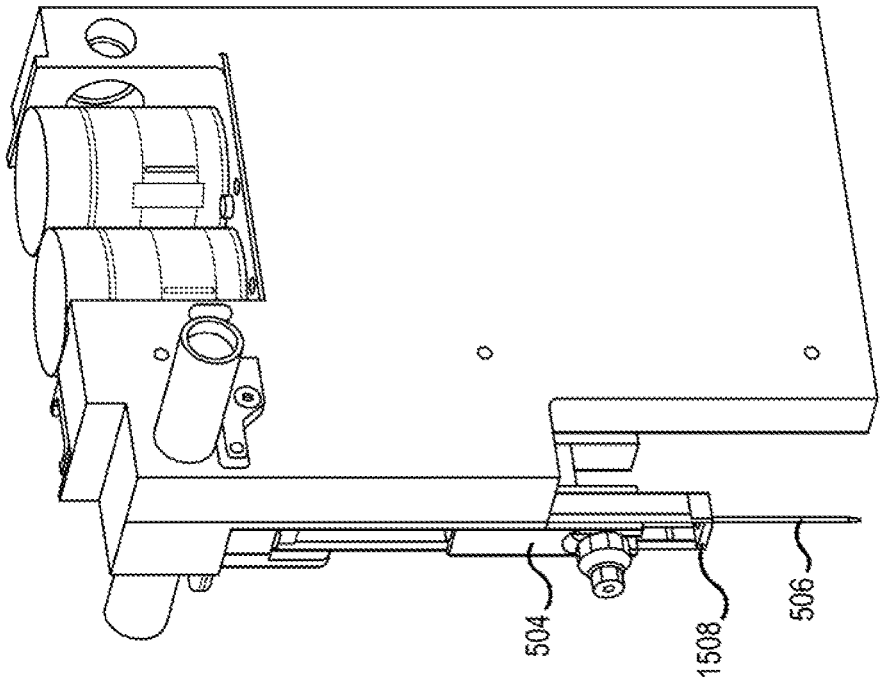
FIG. 19 illustrates a second detailed view of the robot arm of FIG. 18.
Figure 18:
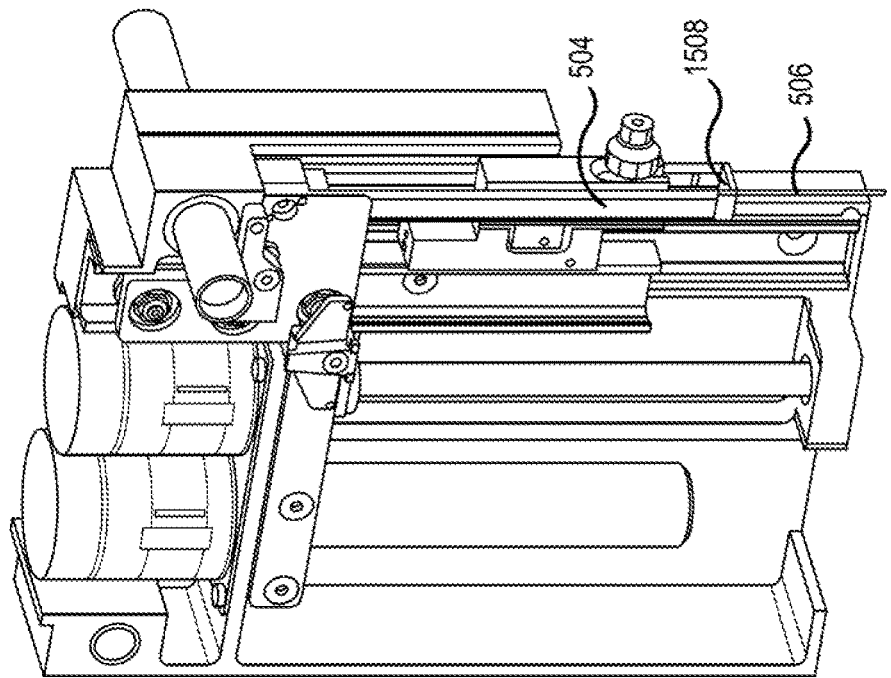
FIG. 18 illustrates a first detailed view of a robot arm of the sample injector of FIG. 17.

FIG. 18 and FIG. 19 show detailed views of the robot arm 1700 wherein the injection needle is denoted with reference numeral 506 and the stripper arrangement with reference numeral 1508.

Figure 20:
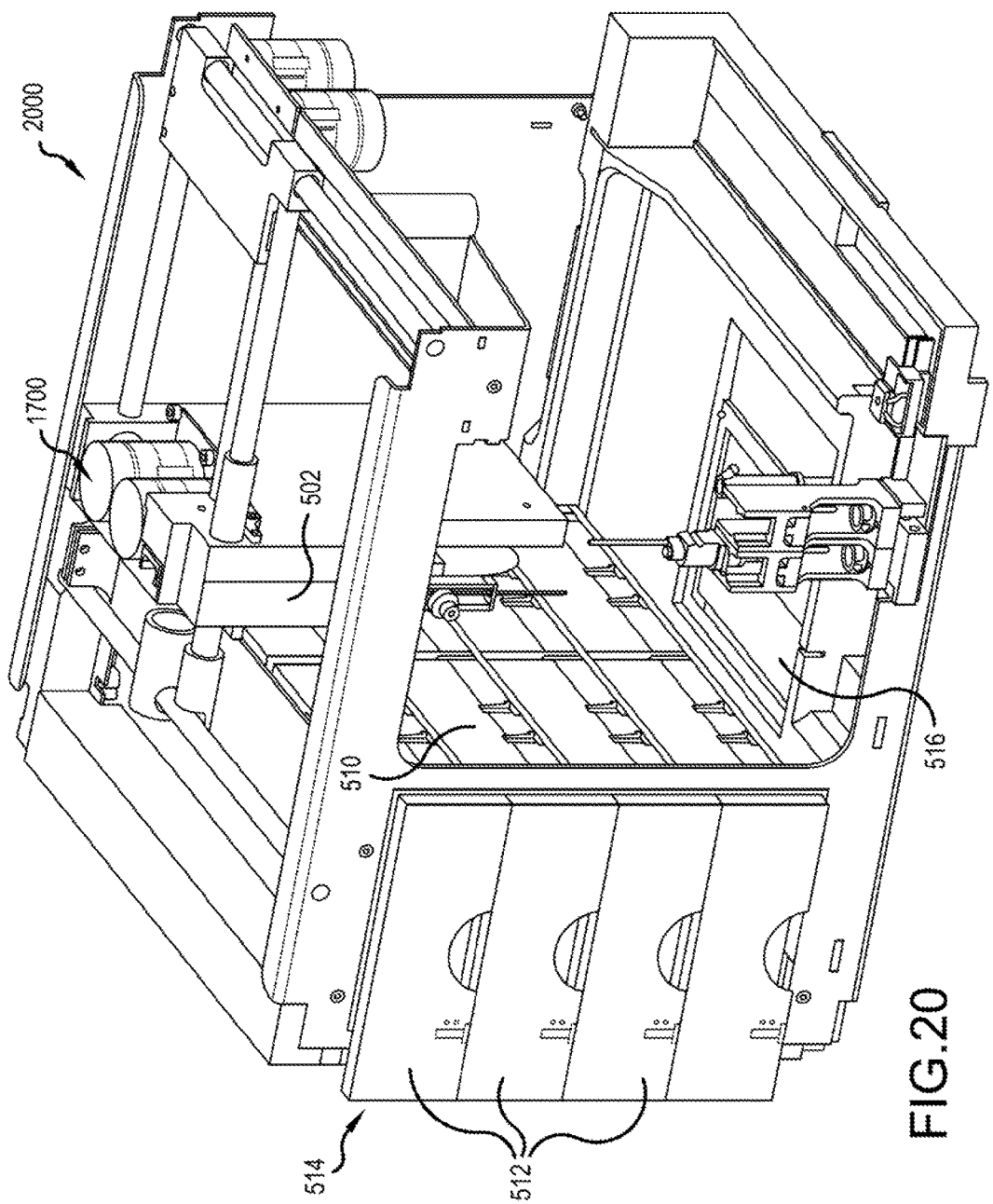
FIG. 20 to FIG. 22 illustrate the sample injector of FIG. 17 in three different operation modes.
Figure 21:
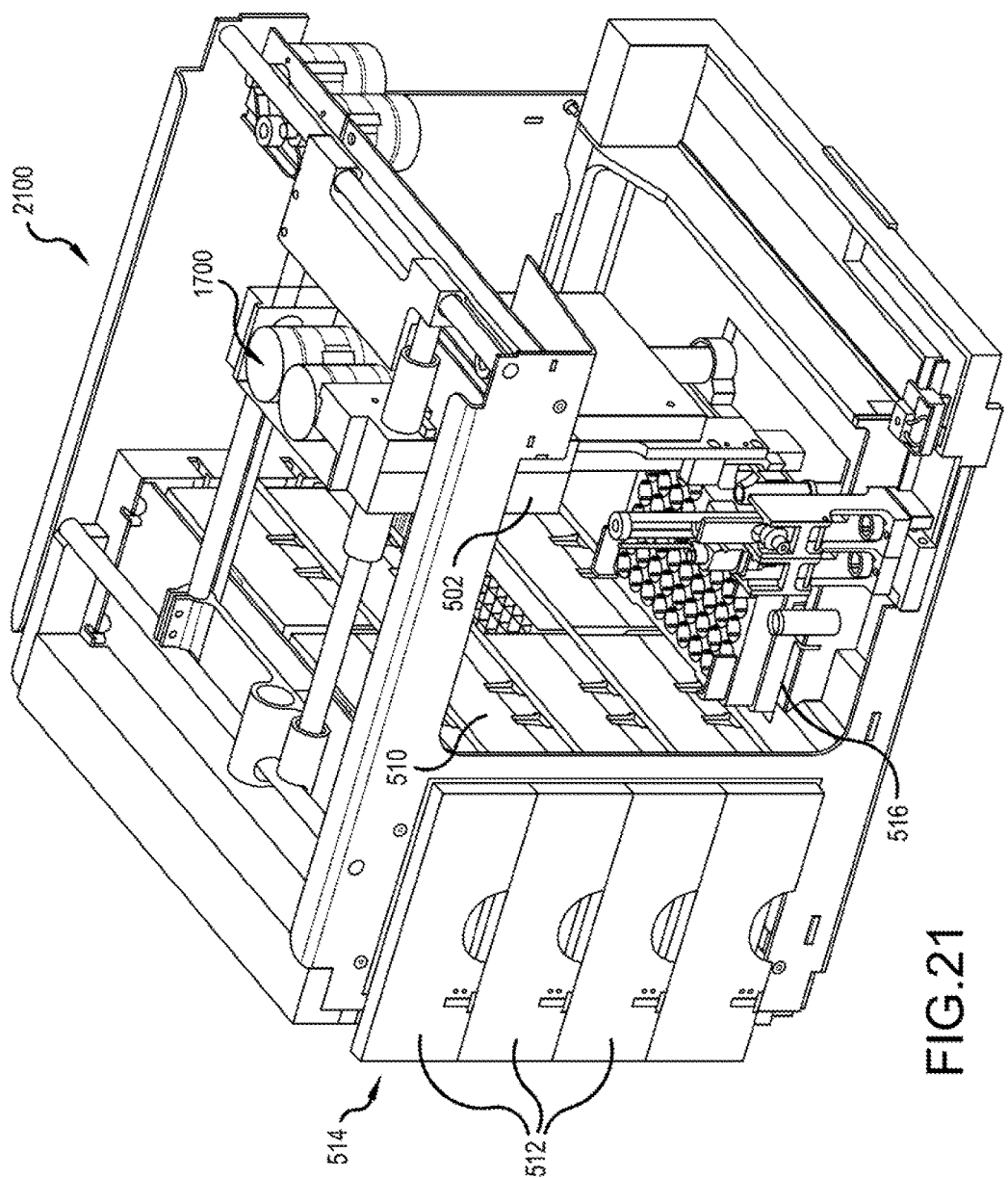
Figure 22:
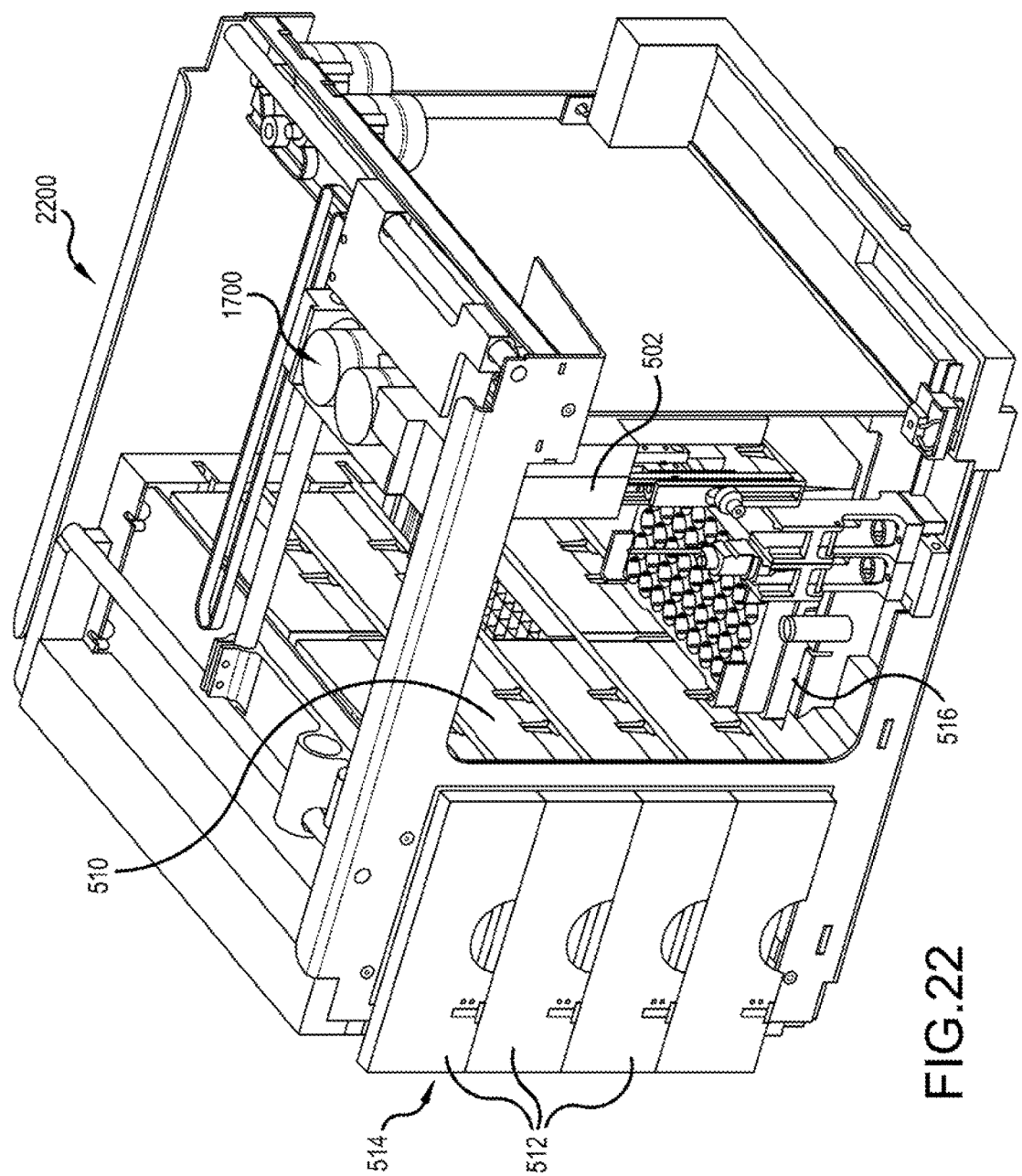

FIG. 20 shows the sample injector of FIG. 17 in a first operation mode 2000 in which the robot moves a palette out of a hotel. FIG. 21 shows the sample injector of FIG. 17 in a second operation mode 2100 in which the robot places the palette on the park station. FIG. 22 shows the sample injector of FIG. 17 in a third operation mode 2200 in which the robot moves the needle to the according sample position to aspirate the sample.

Figure 23:
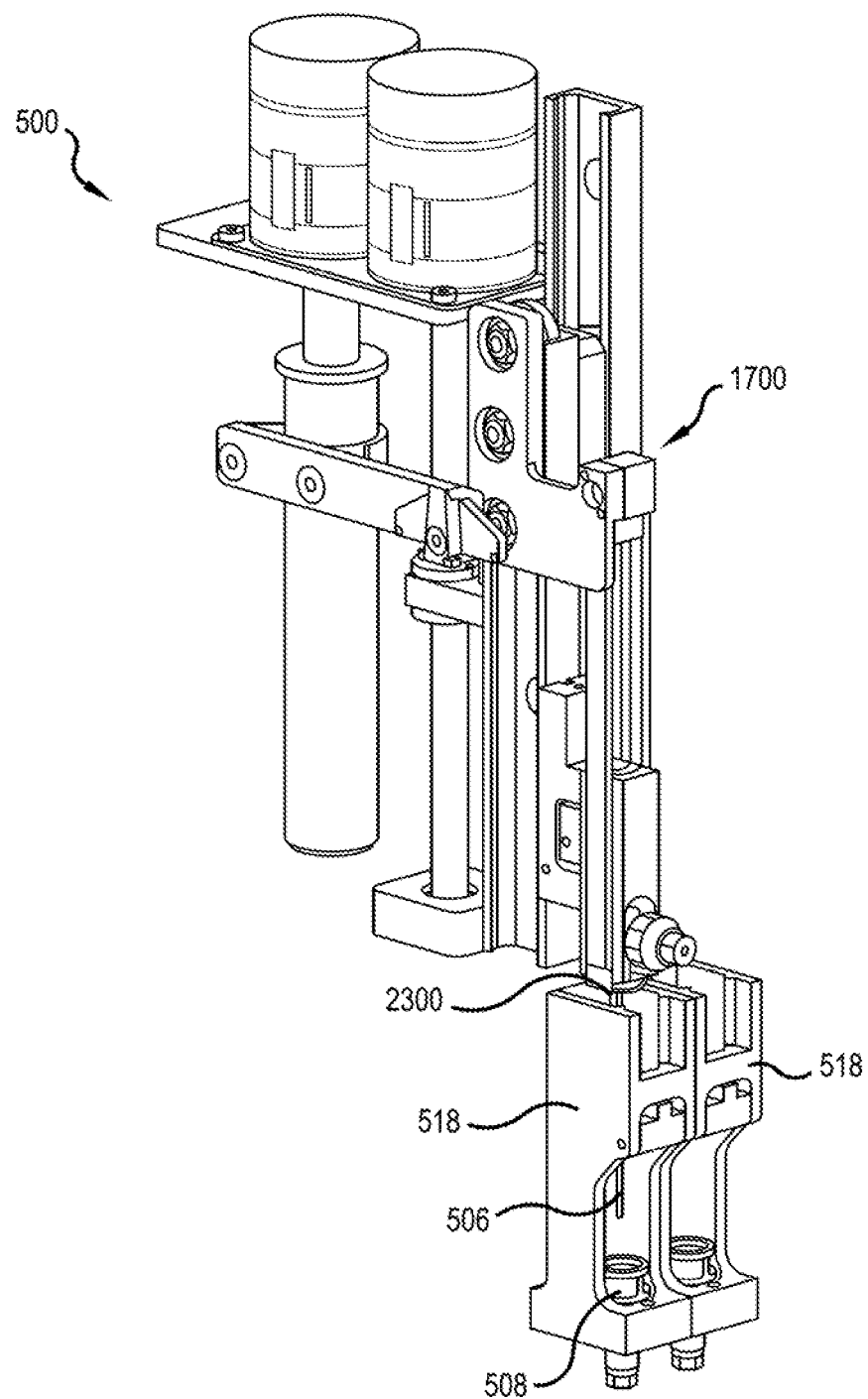
FIG. 23 illustrates a sample injector according to an exemplary embodiment in a three-dimensional view showing details of the sample handling robot arm.

In the following, referring to FIG. 23 to FIG. 25 a sample injector 500 according to still another slightly modified exemplary embodiment will be explained which can be used as a HPLC sample injector with an automatically disconnectable injection needle 506.

A corresponding sample handling robot is able to automatically disconnect the injection needle 506 in a needle park station 518. In this embodiment, the injection needle 506 is coupled to an x, y, z arm via a needle coupler 2300. The needle 506 can be disconnected from the robot arm by a user for exchange purpose or automatically in the needle park station 518. When the needle 506 is disconnected in the needle park station 518, the robot arm is pressing the needle 506 into the needle seat 508 and loads a spring. Then, a locking mechanism may be activated which locks the needle 506 to the needle park station 518 and at the same time opens the lock to the robot arm. Thus, the needle 506 now is sealed in the needle seat 508 by the needle park station 518 and the robot is decoupled from the needle 506. The robot now is able to do other tasks during analysis.

Next, a force amplifying by the needle locking mechanism will be explained. To seal the needle 506 in the needle seat 508, typically a sealing force in the range of 50 to 100 N is needed. Typically, the needle 506 is pressed into the seat 508 via the z-axis of the robot. Thus, a minimal force of 50 to 100 N for the z-drive is needed if the needle 506 is directly coupled to the z-axis of the robot. In an embodiment of a needle coupler, a sealing force amplifying is performed during the decoupling of the needle 506 from the robot. Therefore, the force for the z-drive can be reduced to for instance 30 N to 50 N which is a typical force needed for the z-axis to penetrate the septa of the sample vials.

Figure 24:
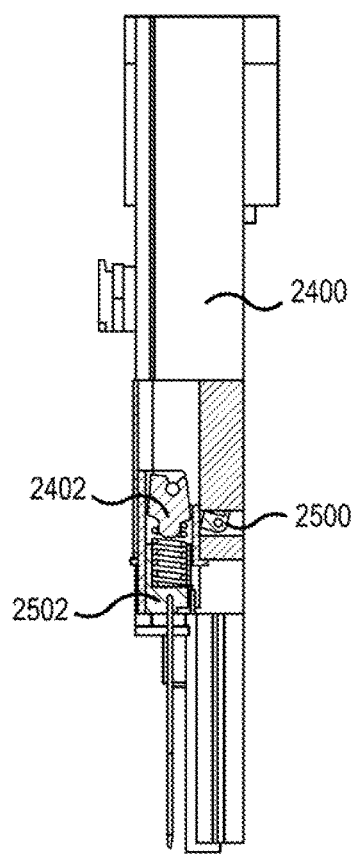
FIG. 24 shows a detailed view of the robot arm of FIG. 24.
Figure 25:
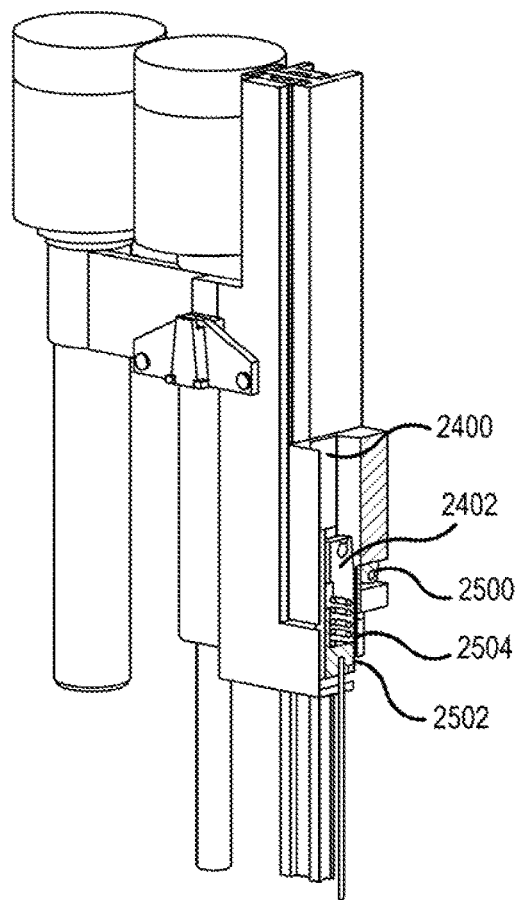
FIG. 25 shows another detailed view of the robot arm of FIG. 24.
Figure 26:
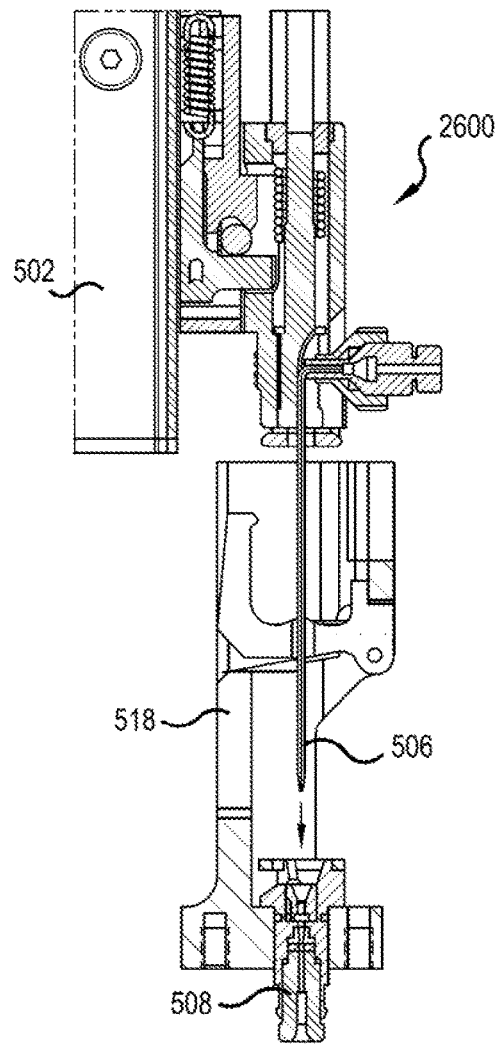
FIG. 26 to FIG. 30 illustrate different operation modes of a needle handling system in which a needle is decoupled from a robot arm and coupled to a needle park station and a seat.

FIG. 24 and FIG. 25 schematically illustrate the function of such a force amplification. The arrangement of FIG. 24 has a robot z-arm 2400, a camshaft 2402 and a camplate. Furthermore, a clamp 2500, a needle holder 2502 and a spring 2504 are shown in FIG. 25.

Inside the needle park station 518, a clamp opens the robot end and at the same time another clamp locks the needle holder 2502 to the needle park station 518. Now, the robot z-arm 2400 is able to move up without a needle 506. During the up movement, the camplate 2404 is activating the camshaft 2402 inside of the needle holder 2502. The camshaft 2402 rotates during the up movement of the robot and loads spring 2504 inside the needle holder 2502 which is pressing the needle 506 down in the needle seat 508.

With this mechanism, a force amplification can be performed. For instance, if the sealing force of 100 N is needed to seal the needle 506 into the needle seat 508, with a camshaft 2402 only ⅕ of the force is needed to load the spring 2504. Of course, a force amplifying during coupling/decoupling the needle 506 to the robot can also be done by another lever mechanism. The camshaft mechanism is only one example.

Advantages of such embodiments of the invention will be explained in the following. A typical analysis time can be in an order of magnitude of 1 min to 60 min. During this time, the needle has to be sealed if the needle seat is flush-through design. Since the robot arm can be decoupled from the needle, the robot is able to do other tasks during this time without disturbing the analysis.

For example, such other tasks which may be done during analysis include the preparation of a next sample plate. If sample plates are stored in a plate hotel, the robot now can place the current sample plate back in the hotel and can prepare the next sample for sample injection. When the next analysis starts, the correct plate already is in place and prepared, which saves time. Another example for such a task is that a next sample can be injected with a second needle. With a second needle and needle park station, the robot already can prepare the next plate, aspirate the sample and place the second needle back in the needle park station. After the analysis is finished in the first needle/needle seat, a valve switches the second needle/needle seat to the analysis path. During analysis with the second needle, the robot handles and injects with the first needle. Therefore, no additional robotic time is added to the sample analysis time. Furthermore, a force amplifying is possible. With for instance a camshaft mechanism, the z-axis of the robot is able to achieve very high sealing loads on the injection needle. Additionally or alternatively, sample preparation and modification can also be performed as an additional task. Since the robot is decoupled from the needle, it can be used for any sample separation and modification, for instance mixing or shaking samples, operating with additional well plate positions like a heater station, barcode reader station or pipetting station. Furthermore, a vial gripper can be foreseen. It is also possible to identify needles or samples with a barcode or a transponder system (such as an RFID system).

Figure 27:
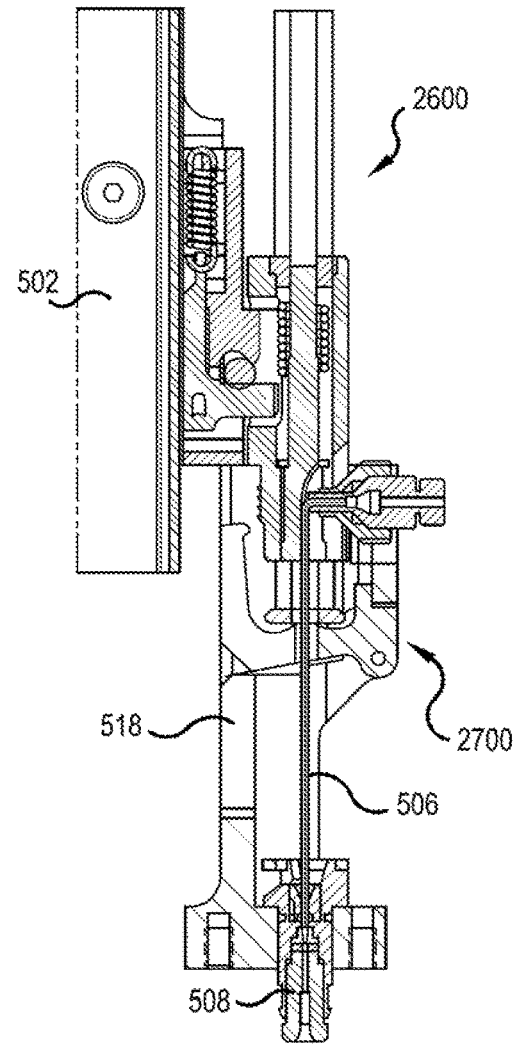
Figure 28:
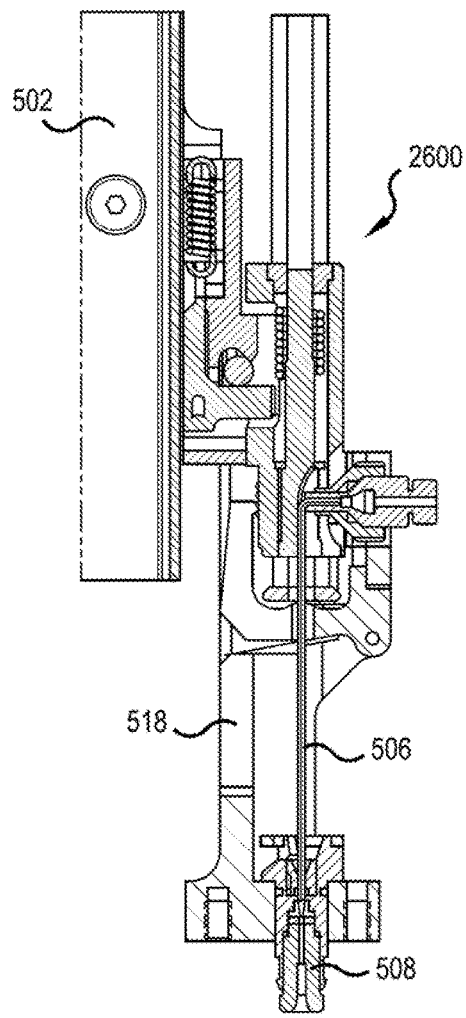
Figure 29:
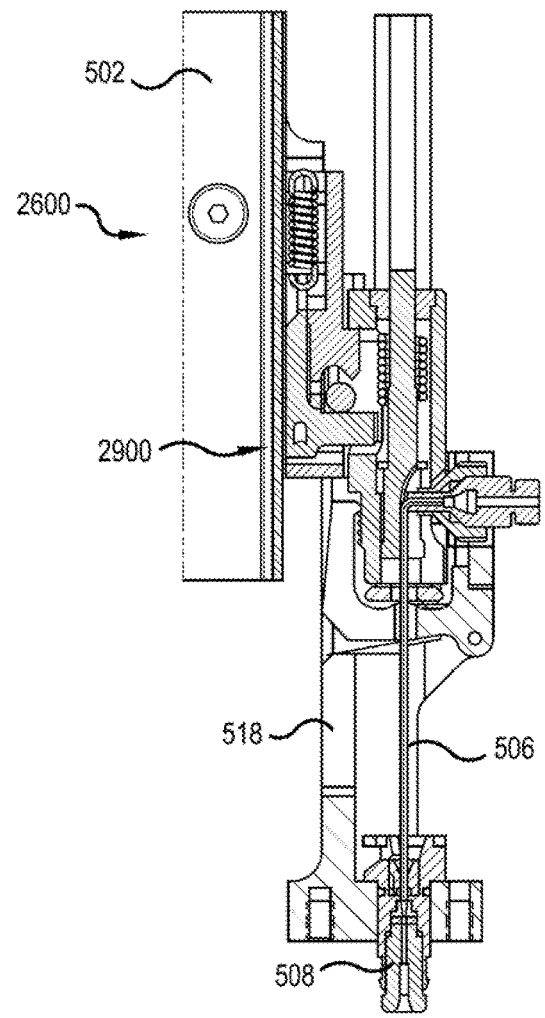
Figure 30:
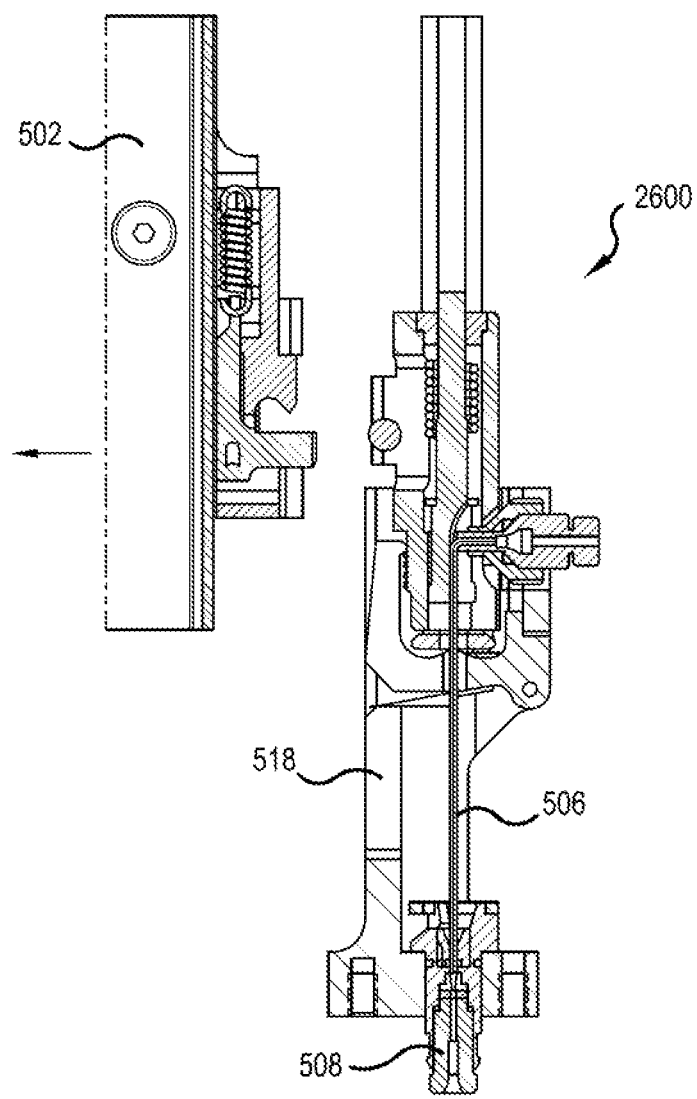

FIG. 26 to FIG. 30 illustrate different operation modes of a needle handling system 2600 in which a needle 506 is decoupled from a robot arm 502 and coupled to a needle park station 518 and a seat 508. The decoupling is performed by a lateral needle decoupling motion In FIG. 26, the robot arm 502 holding the needle 506 approaches the needle park station 518. In FIG. 27, the robot arm 502 has placed the needle 506 in the seat 508 and has accommodated the needle 506 in the needle park station 518. A locking mechanism is opened (see reference numeral 2700). In FIG. 28, the locking mechanism is again closed. In FIG. 29, a coupling mechanism is opened (see reference numeral 2900). In FIG. 30, the robot arm 502 is laterally removed from the needle 506 parked in the needle park station 518.

Referring now in greater detail to the drawings, FIG. 31 depicts a general schematic of a liquid separation system 3110. A pump 3120 receives a mobile phase from a solvent supply 3125, typically via a degasser 3127, which degases and thus reduces the amount of dissolved gases in the mobile phase. The pump 3120—as a mobile phase drive—drives the mobile phase through a separation unit 3130 (such as a chromatographic column) comprising a stationary phase. A sample injector 3140 (compare the detailed description of FIG. 32) can be provided between the pump 3120 and the separation unit 3130 in order to subject or add (often referred to as sample introduction) a sample fluid into the mobile phase. The stationary phase of the separation unit 3130 is configured for separating compounds of the sample liquid. A detector 3150 is provided for detecting separated compounds of the sample fluid. A fractionating unit 3160 can be provided for outputting separated compounds of sample fluid.

While the mobile phase can be comprised of one solvent only, it may also be mixed from plural solvents. Such mixing might be a low pressure mixing and provided upstream of the pump 3120, so that the pump 3120 already receives and pumps the mixed solvents as the mobile phase. Alternatively, the pump 3120 might be comprised of plural individual pumping units, with plural of the pumping units each receiving and pumping a different solvent or mixture, so that the mixing of the mobile phase (as received by the separation unit 3130) occurs at high pressure and downstream of the pump 3120 (or as part thereof). The composition (mixture) of the mobile phase may be kept constant over time, the so called isocratic mode, or varied over time, the so called gradient mode.

A data processing unit 3170, which can be a conventional PC or workstation, might be coupled (as indicated by the dotted arrows) to one or more of the devices in the liquid separation system 3110 in order to receive information and/or control operation. For example, the data processing unit 3170 might control operation of the pump 3120 (for instance setting control parameters) and receive therefrom information regarding the actual working conditions (such as output pressure, flow rate, etc. at an outlet of the pump 3120). The data processing unit 3170 might also control operation of the solvent supply 3125 (for instance setting the solvent/s or solvent mixture to be supplied) and/or the degasser 3127 (for instance setting control parameters such as vacuum level) and might receive therefrom information regarding the actual working conditions (such as solvent composition supplied over time, flow rate, vacuum level, etc.). The data processing unit 3170 might further control operation of the sample injector 3140 (for instance controlling sample injection or synchronization of sample injection with operating conditions of the pump 3120). The separation unit 3130 might also be controlled by the data processing unit 3170 (for instance selecting a specific flow path or column, setting operation temperature, etc.), and send—in return—information (for instance operating conditions) to the data processing unit 3170. Accordingly, the detector 3150 might be controlled by the data processing unit 3170 (for instance with respect to spectral or wavelength settings, setting time constants, start/stop data acquisition), and send information (for instance about the detected sample compounds) to the data processing unit 3170. The data processing unit 3170 might also control operation of the fractionating unit 3160 (for instance in conjunction with data received from the detector 3150) and provide data back.

Reference numeral 3190 schematically illustrates a switchable valve which is controllable for selectively enabling or disabling specific fluidic paths within liquid separation system 3110.

FIG. 32 illustrates constitution of the sample injector 3140 of the liquid separation system 3110 of FIG. 31 having mounted thereon one injection needle cartridge 32300 of a set 32280 of injection needle cartridges 32300 according to an exemplary embodiment.

The one injection needle cartridge 32300 is presently implemented in the liquid separation system 3110 (having particularly the mobile phase drive or pump 3120 and the separation unit 3130, here a separation column) between a sample loop 32204 and a needle seat 32208. The injection needle cartridge 32300 mounted between sample loop 32204 and needle seat 32208 is presently in an active state in terms of sample injecting and belongs to the needle set 32280. Additionally, the needle set 32280 has (in this embodiment) three other injection needle cartridges 32300 which are shown in FIG. 32 as well and are presently in an inactive mode and hence located at a waiting position apart from the sample injector 3140. The different injection needle cartridges 32300 of the needle set 32280 differ basically only concerning their capability of providing different values of a sealing force to be applied between an injection needle 32302 of the injection needle cartridge 32300 and the needle seat 32208, when the respective injection needle cartridge 32300 is in the active state, i.e. mounted on the sample injector 3240. FIG. 32 does not show, how the injection needle cartridges 32300 are hydraulically switched from an inactive state to an active state. Further valves (not shown) may be provided to switch an injection needle cartridge 32300 from an inactive to an active needle configuration.

Each of the injection needle cartridges 32300 comprises a respective injection needle 32302 configured for aspirating sample fluid from a fluid container 32230 when immersed therein. Each injection needle 32302 has an internal lumen through which the sample fluid can flow. Each of each injection needles 32302 is configured for immersing into the fluid container 32230 at a tapering end or tip 32316 which also contributes to the task of providing a high pressure resistant, fluid tight and sealed connection with the seat 32208 and for preventing, inter alia as a result of its tapering shape, an undesired carryover of sample fluid between different sample aspiration and separation cycles. The sample fluid is aspirated when the injection needle 32302 has been moved by a robot arm 32250 of a needle drive system to the fluid container 32230. The sample fluid is injected into the fluidic path between the mobile phase drive 3120 and the separation unit 3130 via the injection needle 32302 when it is sealingly accommodated in the needle seat 32208 and valve 3190 is switched correspondingly. In order to ensure proper sealing between needle 32302 and needle seat 32208, a sealing force generator 32304 is integrated in each of the injection needle cartridges 32300. Each sealing force generator 32304 is configured for exerting an assigned, intrinsically-defined value of the sealing force to the injection needle 32302 for sealingly accommodating the injection needle 32302 when being accommodated in the needle seat 32208. Hence, by providing the needle set 32280 with injection needle cartridges 32300 generating intrinsically different sealing force values, one and the same sample injector 3140 can be used for various applications which may require different values of the sealing force. For instance, a 600 bar application requires a lower sealing force than a 1200 bar application. A biological application using a ceramic needle requires a different sealing force than a standard application using a stainless steel needle, etc. Thus, a user may simply select an appropriate one of the injection needle cartridges 32300 for implementation into the liquid separation system 3110 so as to precisely meet all sealing force related requirements of a certain application.

The sealing force generator 32304 is located completely in an interior of the respective injection needle cartridge 32300, more precisely within a sealing force generator cage 32308 and a needle holder 32306 (holding also the injection needle 32302) of the respective injection needle cartridge 32300. In the injection needle cartridge 32300 being presently in the active mode, the sealing force generator 32304 is a helical spring additionally shielded against an environment by the sealing force generator cage 32308 within which the sealing force generator 32304 is mounted. When that injection needle cartridge 32300 being presently in the active mode is driven into the needle seat 32208 by the robot arm 32250 gripping the injection needle cartridge 32300, the helical spring of this injection needle cartridge 32300 is compressed so that the helical spring applies a back-driving sealing force to the injection needle-needle seat interface, thereby safely sealing the latter in a fluid tight and pressure resistant way.

With regard to the injection needle cartridges 32300 being presently in the waiting position, the injection needle cartridge 32300 of the left hand side and the injection needle cartridge 32300 and the middle also comprise a helical spring as sealing force generator 32304, wherein the different injection needle cartridges 32300 having helical springs as sealing force generator 32304 differ concerning the spring constants. Therefore, each of them provides a different sealing force value. The injection needle cartridge 32300 in the waiting position on the right-hand side of FIG. 32 uses two repelling ferromagnetic permanent magnets 32282 for constituting the sealing force generator 32304 of this injection needle cartridge 32300. When the latter injection needle cartridge 32300 is implemented in the sample injector 3140 and its injection needle 32302 is inserted into the needle seat 32208, the needle 32302 is moved relative to the needle holder 32306 which reduces the distance between the repelling permanent magnets 32282 (one of which being fixedly connected with sealing force generator cage 32308, while the other one is fixedly connected to the needle 32302), so that the repellant force between the permanent magnets 32282 presses the needle 32302 sealingly into the needle seat 32208.

Reference numeral 32314 schematically indicates a fitting member (such as a female piece or a male piece) of each injection needle cartridge 32300 which mates with a counter fitting member 32500 connected to the sample loop 32204 so that connection between this fitting member 32314 and the counter fitting member 32500 forms a fluidic connection between a loop capillary 32260 (or directly the sample loop 32204) and an internal connection capillary 32312 of each injection needle cartridge 32300 connecting the fitting member 32314 fluidically to the lumen in the injection needle 32302. The cooperating fitting members 32314, 32500 may be connected to one another by screwing, a bayonet connection or the like.

As can furthermore be taken from FIG. 32, an RFID tag 32310 is attached to each of the injection needle cartridges 32300 so as to wirelessly communicate with a corresponding RFID reader 32299 of the robot arm 32250. When a robot connection element 32406 of any of the injection needle cartridges 32300 is connected to a corresponding cartridge connection element 32297 of the robot arm 32250, the distance between the respective RFID tag 32310 and the RFID reader 32299 is small enough so that data indicative of the identity of the respective injection needle cartridge 32300 (for instance data indicative of a sealing force value of the corresponding injection needle cartridge 32300) can be transmitted to the robot arm 32250. The color of at least a part of the exterior surface of the injection needle cartridges 32300 may be indicative of the value of the internal sealing force value. For instance, the robot connection element 32406 may have different colors for the different injection needle cartridges 32300 of the set 32280.

The sample loop 32204 is in fluid communication with a port of the valve 3190 and is configured for receiving the sample fluid via the injection needle 32302 which, in turn, receives the sample fluid from the vial or fluid container 32230. The needle 32302 is in fluid communication with the sample loop 32204 via loop capillary 32260. The seat 32208 is configured for selectively receiving the needle 32302 in a fluid-tight manner. Furthermore, an optional seat capillary 32216 is provided which is in fluid communication with the seat 32208 and is in fluid communication with a port 32242 of the valve 3190. Furthermore, a metering device 32210 is shown which is in fluid communication with two ports 32242 of the fluidic valve 3190. An optional flush pump 32212 (such as a 50 bar flush pump) is in fluid communication with a port 32242 in a center of the fluidic valve 3190. Furthermore, an optional wash port 32214 is provided which participates during a needle wash procedure.

The needle 32302 can be moved between the seat 32208 and the fluid container 32230 by the robot arm 32250 (which may be powered by an electric motor or another drive unit, not shown in FIG. 32). When the needle 32302 is immersed in the fluid container 32230, the metering pump 32210 can apply an underpressure to the needle 32302 so that the sample fluid is sucked via the needle 32302 into the loop capillary 32260 and from there into the sample loop 32204. Subsequently, the needle 32302 is driven back into the seat 32208 and the injected fluid is transferred from the sample loop 32204 through the seat 32208 and the valve 3190 into a fluidic path between the mobile phase drive or pump 3120 and the separation column 3130. All the different operation modes involved during this procedure can be carried out by a corresponding switching operation of the fluidic valve 3190. The fluidic valve 3190 comprises two cooperating valve members, one of which having the ports 32242 and the other one having cooperating grooves 32240.

FIG. 33 illustrates a cross-sectional view of an injection needle cartridge 32300 according to an exemplary embodiment. Each of the features of the injection needle cartridge 32300 shown in FIG. 33 may be implemented in FIG. 32 accordingly, and vice versa.

At the sharp end or tip 32316 of the tapering needle 32302, a lumen 33318 extending along the entire injection needle 32302 is exposed to an environment for aspirating sample fluid. FIG. 33 shows in detail that the casing or housing of the injection needle cartridge 32300 comprises two components, i.e. needle holder 32306 as inner, first component accommodating a part of the injection needle 32302 and a part of the capillary 32312, and the sealing force generator cage (here: spring cage) 32308 as a second component in which a helical spring as sealing force generator 32304 is completely accommodated and shielded with regard to the environment.

Thus, the sealing force generator 32304 is here configured as preloaded spring included in the injection needle cartridge 32300 which determines the quantity of the sealing force of the specific injection needle 32302. If the injection needle 32302 has to be changed in the liquid chromatography system as liquid separation system 3110, the complete injection needle cartridge 32300 including sealing force generator cage 32308 is exchanged. Therefore, the sealing force value and orientation can be adapted to the requirements of the needle material, needle geometry and maximum system pressure without changing the algorithm of the needle drive mechanism, here formed by robot arm 33250 and connected drive (not shown in FIG. 33).

The capillary 32312 may be welded into the needle 32302, for instance by laser welding. To render the welding procedure efficient and successful, the capillary 32312 and the needle 32302 may be made of the same material. The spring cage 32308 may be made for instance of stainless steel, silver or a plastic material. As can be taken from FIG. 32, the capillary 32312 is hydraulically connected to the loop capillary 32260 via the cooperating fitting members 32314, 32500.

FIG. 34 illustrates a cartridge adapter 34400 of a sample injector 3140 according to an exemplary embodiment configured for receiving the injection needle cartridge 32300 of FIG. 33. FIG. 34 shows the arrangement of cartridge adapter 34400 and injection needle cartridge 32300 in a mutually locked state. FIG. 35 illustrates the cartridge adapter 34400 of FIG. 34 receiving the injection needle cartridge 32300 of FIG. 33 in an unlocked state.

In the embodiment shown in FIG. 34 and FIG. 35, the injection needle cartridge 32300 is configured to be inserted into the cartridge adapter 34400 for connection, in turn, to the robot arm 32250 via a robot connection element 32406, as described below in more detail. However, as an alternative, the spring cage 32308 itself may be used as a component to be gripped by the robot arm 32250. For this purpose, an appropriately shaped and dimensioned grip support element (not shown) may be integrally formed with the sealing force generator cage 32308. In such an embodiment, the cartridge locking mechanism 34404 and the robot connection element 32406 can be omitted to obtain a particularly compact device.

Coming back to the embodiment of FIG. 34 and FIG. 35, the sample injector 3140 comprises the cartridge adapter 34400 which is configured for detachably receiving the injection needle cartridge 32300 and is configured for being attached, with the injection needle cartridge 32300 being mounted, to the handling robot 32250. The cartridge adapter 34400 has a needle protection mechanism 34402 which is configured for operating the injection needle 32302 selectively in a protected state in which the tip 32316 of the injection needle 32302 is accommodated within the cartridge adapter 34400 (protected state not shown). In such a protected state, a user is protected from injury by the sharp tip 32316, and the needle 32302 is protected against damage. The needle protection mechanism 34402 is also configured for alternatively operating the injection needle 32302 in an active state, see FIG. 4 and FIG. 5, in which the tip 32316 of the injection needle 32302 protrudes beyond the cartridge adapter 34400. In the active state, the injection needle 32302 is ready for aspirating sample fluid via tip 32316. In the shown embodiment, the needle protection mechanism 34402 is formed by a member having two (or more) parallel legs 34408 between which the injection needle cartridge 32300 can be located and moved upwardly or downwardly. At their lower ends, the legs 34408 are connected to one another via an end plate 34410. The end plate 34410 has a through hole 34412 through which the needle 32302 can penetrate. In an expanded state of the needle 32302, the needle 32302 extends through the through hole 34412 and is exposed to an environment for aspirating fluid sample or for being inserted into the seat 32208. In the retracted state of the needle 32302, the needle 32302 is completely located between the legs 34408 and does not extend through the through hole 34412. The needle protection mechanism 34402 together with the end plate 34410 can be slid relatively to the injection needle 32302 (or vice versa) to convert the injection needle 32302 between the protected state and the active state. The injection needle 32302 can be brought into a stable configuration in both the protected state and the active state.

Additionally, the cartridge adapter 34400 comprises a cartridge locking mechanism 34404 in the form of a lever-based clamping mechanism which is configured for detachably locking the injection needle cartridge 32300 with the cartridge adapter 34400 by a latch 35502. FIG. 34 shows the lever of the cartridge locking mechanism 34404 in a locked state in which the injection needle cartridge 32300 is rigidly locked to the cartridge adapter 34400. FIG. 35 shows the lever of the cartridge locking mechanism 34404 in an unlocked state in which the injection needle cartridge 32300 is not locked to the cartridge adapter 34400, and can be inserted or removed in this state.

A sample injector 3140 corresponding to FIG. 34 and FIG. 35 furthermore comprises a robot connection element 32406 which is laterally connected at the cartridge adapter 34400 and is configured for attaching the cartridge adapter 34400 to the handling robot 32250 by sliding the robot connection element 32406 on the handling robot 32250. Reference numeral 34420 shows a permanent magnet used for simplifying the sliding connection of the arrangement shown in FIG. 34 and FIG. 35 to the robot arm 32250 making use of a supporting, attracting magnetic force. The robot arm 32250 has a corresponding permanent magnet (not shown) which attracts the permanent magnet 34420 of the cartridge adapter 34400 and therefore promotes correct orientation of the cartridge adapter 34400 relative to the robot arm 32250.

The arrangement of FIG. 34 can further be configured for stripping off a vial or any other fluid container 32230 from the injection needle 32302 after the injection needle 32302 has aspirated sample fluid by immersing into the vial or other fluid container 32230.

FIG. 36 illustrates a cartridge adapter 34400 presently receiving an injection needle cartridge 32300 together with a robot connection element 32406 according to an exemplary embodiment in an operation mode in which the injection needle 32302 is exposed to an environment. In the shown state, the end tip 32316 of the injection needle 32302 protrudes over the needle protection mechanism 34402 to thereby enable sample aspiration.

FIG. 37 shows a three-dimensional view of the injection needle cartridge 32300 according to an exemplary embodiment implemented in FIG. 36. The integrally formed structure of FIG. 37 is a consumable which can be, as a whole, connected to or separated from the cartridge adapter 34400.

Figure 38:
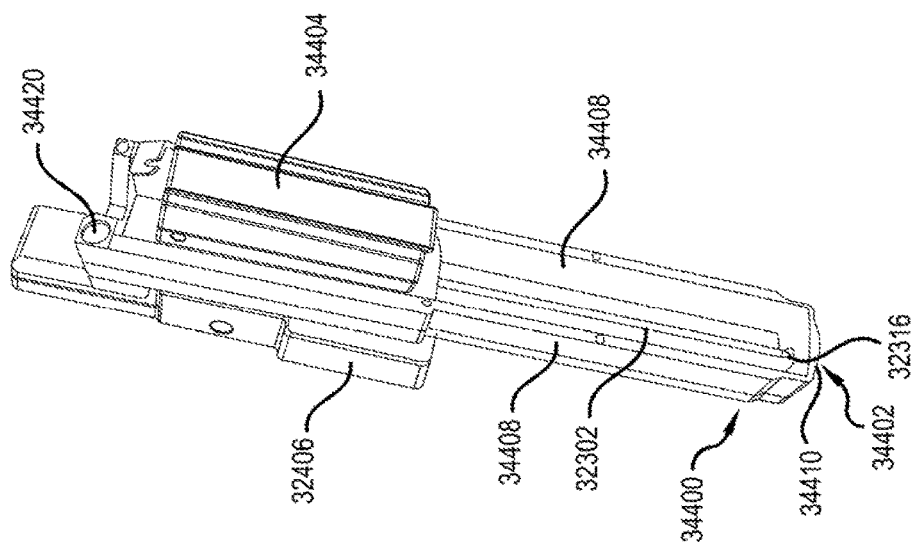
FIG. 38 illustrates the cartridge adapter of FIG. 6 in an operation mode in which the injection needle is retracted into an interior of the cartridge adapter.

FIG. 38 illustrates the robot connection element 32406 of FIG. 36 in an operation mode in which the injection needle 32302 is retracted into an interior of the cartridge adapter 34400. Thus, the tip 32316 does not protrude over the end plate 34410 of the needle protection mechanism 34402 and is therefore prevented from injuring a user and from being damaged by a mechanical impact from the environment.

Figure 39:
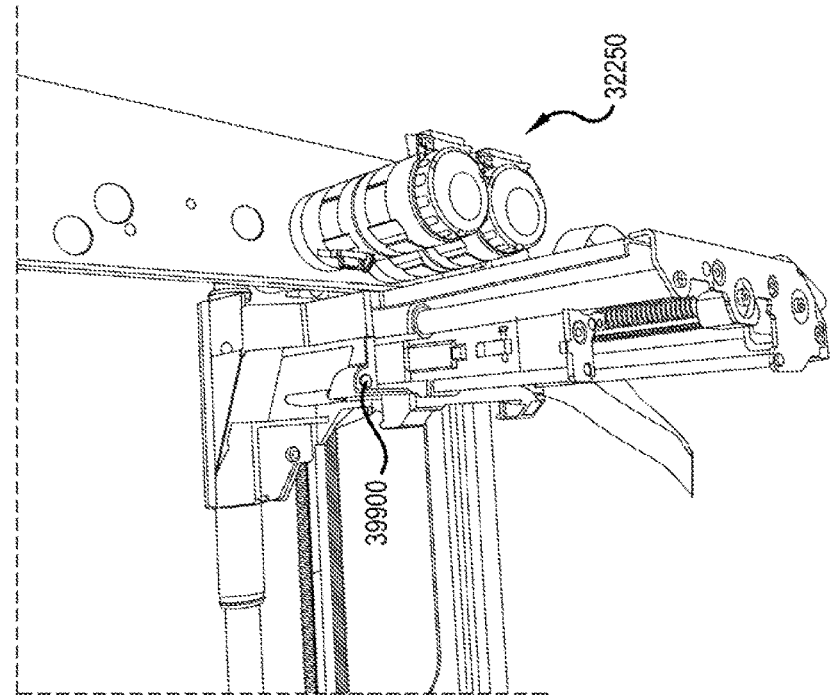
FIG. 39 illustrates a robot arm for mounting a cartridge adapter according to an exemplary embodiment.

FIG. 39 illustrates a robot arm 32250 for mounting a cartridge adapter 34400 according to an exemplary embodiment. The arrangement of FIG. 38 can be mounted on the robot arm 32250 by sliding the robot connection element 32406 onto a corresponding counterpart on the robot arm 32250 to a state in which the permanent magnet 34420 of the cartridge adapter 34400 is in attracting alignment with a permanent magnet 39900 of the robot arm 32250.

It should be noted that the term "comprising" does not exclude other elements or features and the term "a" or "an" does not exclude a plurality. Also elements described in association with different embodiments may be combined. It

The invention claimed is:

1. An injection needle cartridge for a sample injector for injecting a sample fluid into a mobile phase in a fluidic path of a fluid separation system between a mobile phase drive and a separation unit, the injection needle cartridge comprising:
an injection needle configured for aspirating the sample fluid from a fluid container when the injection needle has been moved to the fluid container, and for injecting aspirated sample fluid into the fluidic path when the injection needle is sealingly accommodated in a needle seat; and
a sealing force generator integrated in the injection needle cartridge and configured for applying a sealing force to the injection needle for sealingly accommodating the injection needle in the needle seat; and
a housing accommodating at least part of the injection needle and at least part of the sealing force generator, wherein the injection needle cartridge is configured for being substitutably mountable on and demountable from a handling robot of the sample injector for handling the injection needle cartridge between the fluid container and the needle seat.

2. The injection needle cartridge of claim 1, wherein the sealing force generator comprises an elastic member.

3. The injection needle cartridge of claim 2, wherein the elastic member comprises a sealing force spring, and at least part of the sealing force spring is arranged to circumferentially surround at least part of the injection needle.

4. The injection needle cartridge of claim 2, wherein the elastic member is supported between the injection needle and the housing.

5. The injection needle cartridge of claim 2, wherein the elastic member is mounted so as to be compressed upon pressing the injection needle against the needle seat.

6. The injection needle cartridge of claim 2, wherein the elastic member is mounted in a pre-biased state.

7. The injection needle cartridge of claim 2, wherein the elastic member comprises a component selected from the group consisting of: a sealing force spring; and an elastomeric element.

8. The injection needle cartridge of claim 1, wherein the sealing force generator comprises a component selected from the group consisting of: a magnetic sealing force generator generating a magnetic sealing force: and an electric sealing force generator generating an electric sealing force.

9. The injection needle cartridge of claim 1, comprising a readable marker configured to indicate a sealing force value provided by the sealing force generator.

10. The injection needle cartridge of claim 9, wherein the readable marker comprises a machine-readable marker.

11. The injection needle cartridge of claim 9, wherein the readable marker comprises a human-readable marker.

12. The injection needle cartridge of claim 1, comprising a capillary in fluid communication with the injection needle, the capillary being welded to the injection needle within a housing of the injection needle cartridge.

13. The injection needle cartridge of claim 1, comprising a fitting member in fluid communication with the injection needle and being configured to provide a fluid-tight fluid communication interface upon being connected with a corresponding fitting member counterpart in fluid communication with a loop capillary of the sample injector.

14. The injection needle cartridge of claim 1, wherein the sealing force generator is configured for applying a sealing force with a predefined value when the injection needle is accommodated in the needle seat.

15. The injection needle cartridge of claim 1, further comprising a robot connection element laterally connected at the housing and configured for attaching the injection needle cartridge to the handling robot by sliding the robot connection element on the handling robot.

16. A needle set comprising a plurality of injection needle cartridges of claim 1, wherein different ones of the injection needle cartridges provide different sealing force values.

17. The needle set of claim 16, wherein the injection needle of one of the injection needle cartridges is a ceramic needle, and the injection needle of another one of the injection needle cartridges is a metallic needle.

18. A sample injector for injecting a sample fluid into a mobile phase in a fluidic path of a fluid separation system between a mobile phase drive and a separation unit, the sample injector comprising:
an injection needle cartridge of claim 1;
a needle seat configured for sealingly accommodating the injection needle of the injection needle cartridge and providing fluid communication with the fluidic path, wherein the sealing force generator of the injection needle cartridge provides the sealing force when the injection needle is accommodated in the needle seat;
a handling robot on which the injection needle cartridge is mountable or mounted and being configured for moving the injection needle between a fluid container containing the sample fluid and the needle seat.

19. The sample injector of claim 18, comprising a cartridge adapter configured for detachably receiving the injection needle cartridge and being configured for being attached to the handling robot.

20. The sample injector of claim 19, wherein the cartridge adapter comprises a needle protection mechanism configured for operating the injection needle selectively in a protected state in which at least a tip of the injection needle is accommodated within the cartridge adapter or in an active state in which at least the tip of the injection needle protrudes beyond the cartridge adapter.

21. The injection needle cartridge of claim 20, wherein the needle protection mechanism is configured for forcing the injection needle into the protected state upon demounting the injection needle cartridge from the handling robot and/or for forcing the injection needle into the active state upon mounting the injection needle cartridge on the handling robot.

22. The sample injector of claim 19, wherein the cartridge adapter comprises a cartridge locking mechanism configured for detachably locking the injection needle cartridge to the cartridge adapter.

23. The sample injector of claim 19, comprising a robot connection element laterally connected at the cartridge adapter and configured for attaching the cartridge adapter to the handling robot by sliding the robot connection element on the handling robot.

24. The sample injector of claim 18, wherein the sealing force generator, the injection needle and the needle seat are configured to cooperate so that the injection needle is adapted to be accommodated in the needle seat at a pressure of 1200 bar.

25. The sample injector of claim 18, wherein the handling robot is free of a sealing force generator.

26. A fluid separation system for separating compounds of a sample fluid in a mobile phase, the fluid separation system comprising:
   a mobile phase drive configured to drive the mobile phase through the fluid separation system;
   a separation unit, particularly a chromatographic column, configured for separating compounds of the sample fluid in the mobile phase; and
   a sample injector according to claim 18 configured for injecting the sample fluid in the fluidic path between the mobile phase drive and the separation unit.

27. A method of operating a sample injector with an injection needle cartridge of claim 1 for injecting a sample fluid into a mobile phase in a fluidic path of a fluid separation system between a mobile phase drive and a separation unit, the method comprising:
   substitutably mounting the injection needle cartridge on a handling robot of the sample injector;
   moving the injection needle cartridge by the handling robot to a fluid container containing the sample fluid;
   aspirating the sample fluid from the fluid container via the injection needle into a sample loop of the sample injector;
   moving the injection needle cartridge by the handling robot to the needle seat and sealingly accommodating the injection needle in the needle seat by applying a sealing force generated by the sealing force generator;
   injecting the aspirated sample fluid from the sample loop via the injection needle into the fluidic path when the injection needle is sealingly accommodated in the needle seat.

\* \* \* \* \*